United States Patent
Åkerstrom et al.

(10) Patent No.: US 10,226,507 B2
(45) Date of Patent: Mar. 12, 2019

(54) ALPHA-1-MICROGLOBULIN FOR USE IN THE TREATMENT OF MITOCHONDRIA-RELATED DISEASES

(71) Applicant: A1M Pharma AB, Lund (SE)

(72) Inventors: Bo Åkerstrom, Lund (SE); Magnus Gram, Oxie (SE); Lena Rosenlöf, Hörby (SE)

(73) Assignee: A1M PHARMA AB, Lund (SE)

( * ) Notice: Subject to any disclaimer, the term of this patent is extended or adjusted under 35 U.S.C. 154(b) by 0 days.

(21) Appl. No.: 14/423,260

(22) PCT Filed: Sep. 4, 2013

(86) PCT No.: PCT/EP2013/068270
§ 371 (c)(1),
(2) Date: Feb. 23, 2015

(87) PCT Pub. No.: WO2014/037390
PCT Pub. Date: Mar. 13, 2014

(65) Prior Publication Data
US 2015/0258171 A1 Sep. 17, 2015

(30) Foreign Application Priority Data

Sep. 5, 2012 (DK) ................................ 2012 70538
Sep. 12, 2012 (DK) ................................ 2012 70557

(51) Int. Cl.
*A61K 38/17* (2006.01)

(52) U.S. Cl.
CPC .......... *A61K 38/1722* (2013.01); *A61K 38/17* (2013.01)

(58) Field of Classification Search
None
See application file for complete search history.

(56) References Cited

U.S. PATENT DOCUMENTS

| | | | |
|---|---|---|---|
| 8,568,999 B2 * | 10/2013 | Hansson | 435/7.1 |
| 2011/0177051 A1 * | 7/2011 | Galski-Lorberboum | C12Y 108/01004 424/94.3 |
| 2011/0190208 A1 | 8/2011 | Akerstrom et al. | |

FOREIGN PATENT DOCUMENTS

| WO | WO 2008/098734 | * | 8/2008 |
|---|---|---|---|
| WO | WO 2010/006809 A3 | | 1/2010 |

OTHER PUBLICATIONS

Hart et al ('Antioxidant treatment of patients with Friedreich ataxia' Arch Neurol v62 Apr. 2005 pp. 621-626).*
Christodoulou J ('Genetic defects causing mitochondrial respiratory chain disorders and disease' Human Reproduction v15(2) 2000 pp. 28-43).*
National Institute of Neurological Disorders and Stroke (retrieved from http://www.ninds.nih.gov/disorders/friedreichs_ataxia/detail_friedreichs_ataxia.htm on Dec. 9, 2015, 7 pages).*
United Mitochondrial Disease Foundation (retrieved from http://www.umdf.org/site/pp.aspx?c=8qKOJ0MvF7LUG&b=7934635 on Dec. 9, 2015, 6 pages).*
Lodi et al. ('Friedreich's ataxia: from disease mechanisms to therapeutic interventions' Antioxidants & redox signaling v8 2006 pp. 438-443).*
Olsson et al. ('Up-regulation of A1M/alpha1-microglobulin in skin by heme and reactive oxygen species gives protection from oxidative damage' Plos One v6(11) Nov. 2011 e27505 pp. 1-10).*
Maneiro et al. ('Mitochondrial respiratory activity is altered in osteoarthritic human articular chondrocytes' Arthritis and Rheumatism v48(3) Mar. 2003 pp. 700-708) (Year: 2003).*
Illsinger et al. ('Preeclampsia and HELLP syndrome: impaired mitochondrial function in umbilical endothelial cells' Reproductive Sciences v17(3) Mar. 2010 pp. 219-226) (Year: 2010).*
PubMed entry (retrieved from https://www.ncbi.nlm.nih.gov/pubmed/?term=pathological+conditions+involving+extracelular+hemoglobin on May 1, 2018, 2 pages) (Year: 2018).*
Olsson et al., "The Radical-Binding Lipocalin A1M Binds to a Complex I Subunit and Protects Mitochondrial Structure and Function," Antioxidants and Redox Signaling, vol. 18, No. 16, pp. 2017-2028, Jan. 4, 2013.
Olsson et al., "Pathological conditions involving extracellular hemoglobin: molecular mechanisms, clinical significance, and novel therapeutic opportunities for $\alpha_1$-Microglobulin,"Antioxidants and Redox Signaling, vol. 17, No. 5, pp. 813-846, Sep. 1 2012.
May et al., "Perfusion of human placenta with hemoglobin introduces preeclampsia-like injuries that are prevented by macroglobulin," Placenta, vol. 32, No. 4, pp. 323-332, Jan. 31, 2011.
Akerstrom et al., "The lipocalin $\alpha_1$-microglobulin has radical scavenging activity," Journal of Biological Chemistry, vol. 282, pp. 31493-31503, Jan. 1, 2007.
Olsson et al., "The lipocalin $\alpha_1$-Microglobulin Protects Erythroid K562 Cells Against Oxidative Damage Induced by Heme and Reactive Oxygen Species," Free Radical Research, vol. 42, No. 8, pp. 725-736, Aug. 1, 2008.
International Search Report dated Nov. 7, 2013 in application No. PCT/EP2013/068270.
Olsson et al., "Antioxidants, Nutrition and Novel Therapiest 2: The endogenous radical scavenger A1M binds to complex I and protects mitochondrial structure and function: an novel cellular protective mechanism," Free Radical Biology and Medicine, vol. 53, Suppl. 1, p. S43, Sep. 2012.
Bai et al., "Restoration of Mitochonrdial Function in Cells with Complex I Deficiency,"Ann. N.Y. Acad. Sci., vol. 1042, pp. 25-35, 2005.
Unknown, Clinical Neuroscience, vol. 24, No. 6, pp. 671-672, 2006.
Japanese Office Action dated Feb. 14, 2017 in application No. JP 2015-530375.

(Continued)

*Primary Examiner* — Karlheinz R. Skowronek
*Assistant Examiner* — Ronald T Niebauer
(74) *Attorney, Agent, or Firm* — Foley & Lardner LLP

(57) ABSTRACT

The present invention relates to alpha-1-microglobulin for use in the treatment of a mitochondria-related disease.

12 Claims, 13 Drawing Sheets
Specification includes a Sequence Listing.

(56) References Cited

OTHER PUBLICATIONS

Triepels et al., "Respiratory chain complex I deficiency," Am. J. Med. Genet., vol. 106, No. 1, pp. 37-45, 2001, Abstract.
Hermansen et al., "Respiratory Distress in the Newborn," American Family Physician. vol. 76, No. 7, pp. 987-994, Oct. 2007.
Cederland et al., "Vitreous levels of oxidative stress biomarkers and the radical-scavenger a1-microglobulin/A1M in human rhegmatogenous retinal detachment" Graefes Arch. Clin. Exp. Ophthalmol., (2013) vol. 251 pp. 725-732 (Published Online Jul. 25, 2012).
Kobayashi et al., "A Case of Leber's Hereditary Optic Neuropathy in a Female Patient with the Recrudescence of Hyperthyroidism", Nippon Ganka Gakkai Zasshi, (Nov. 2007) vol. 111, pp. 905-910.

* cited by examiner

Figure 1:
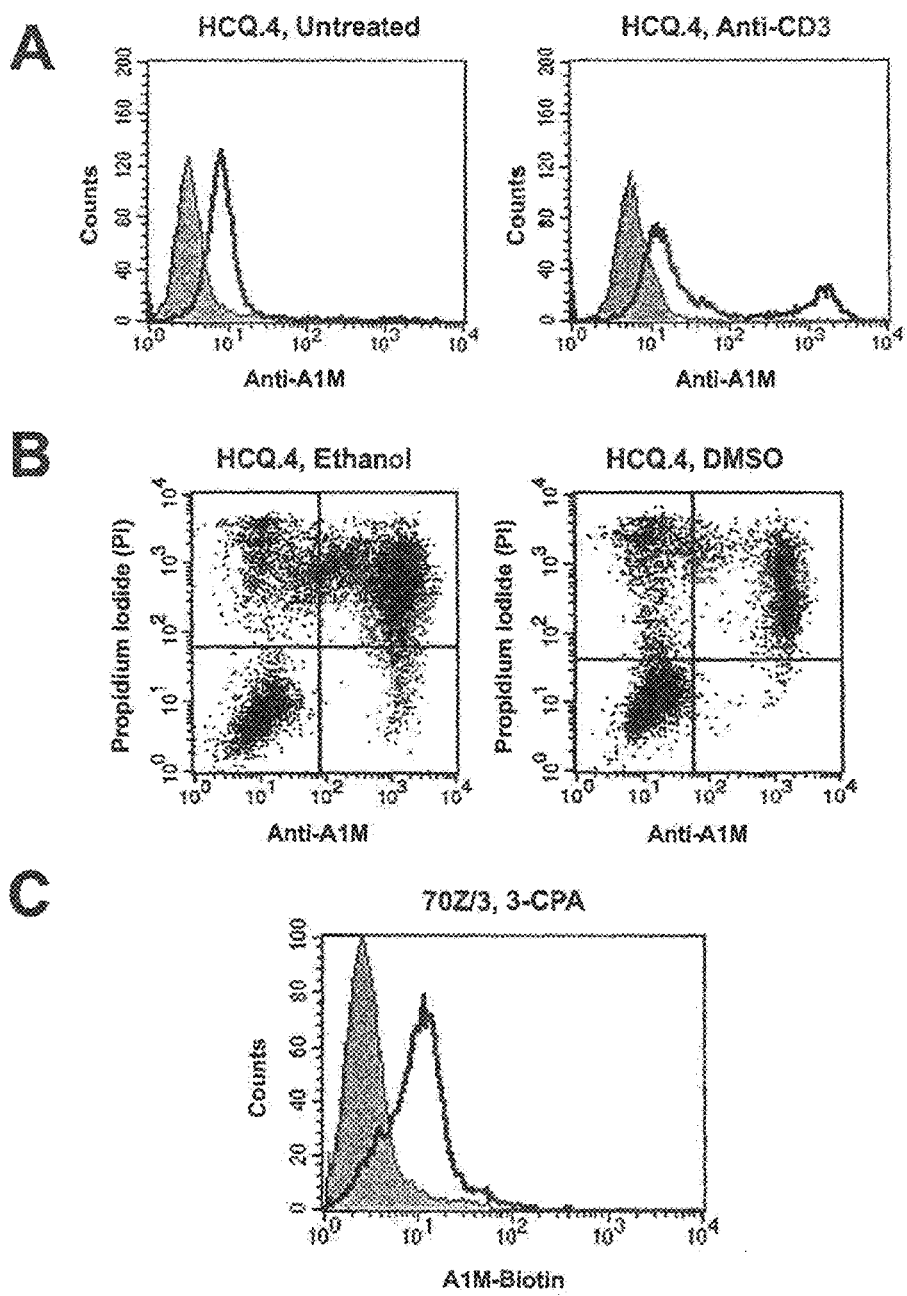

Figure 1 (continued)
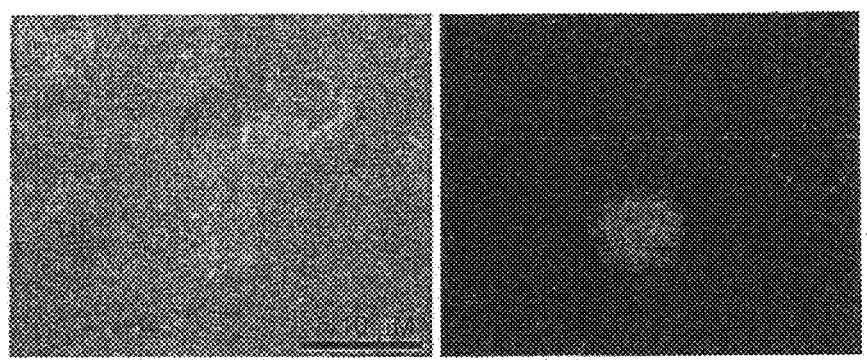
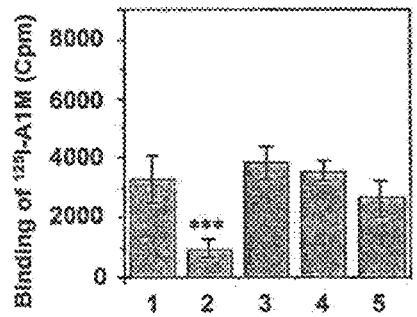
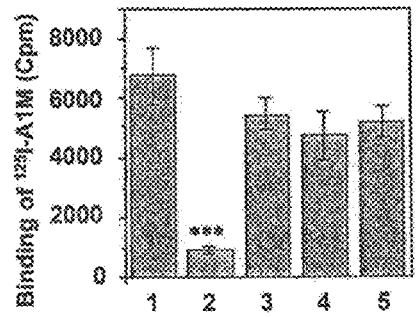

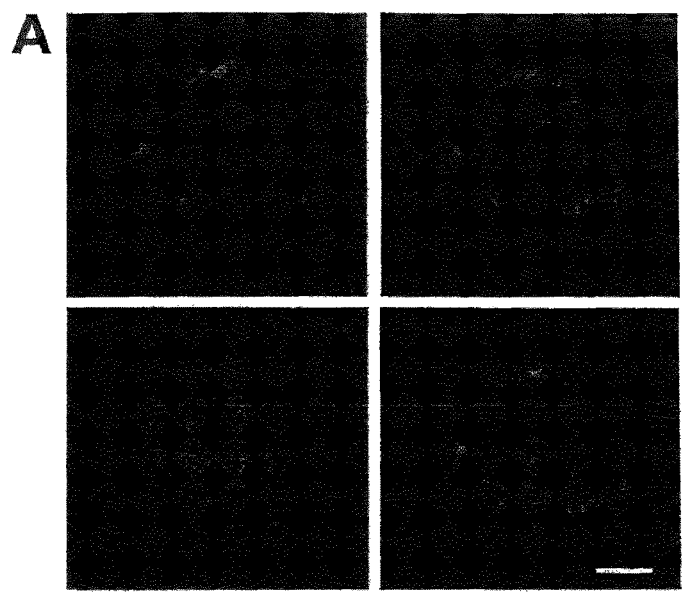
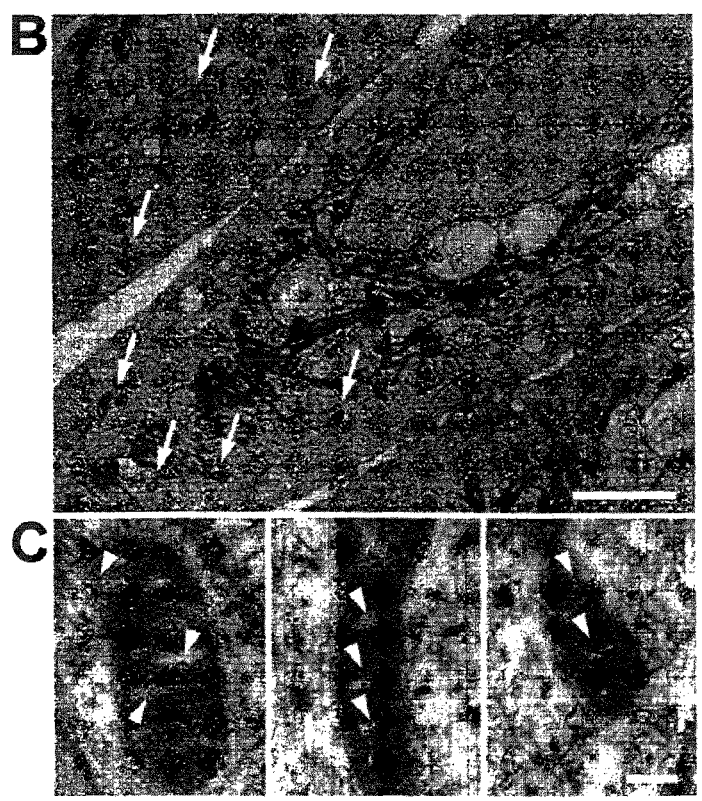
Figure 3

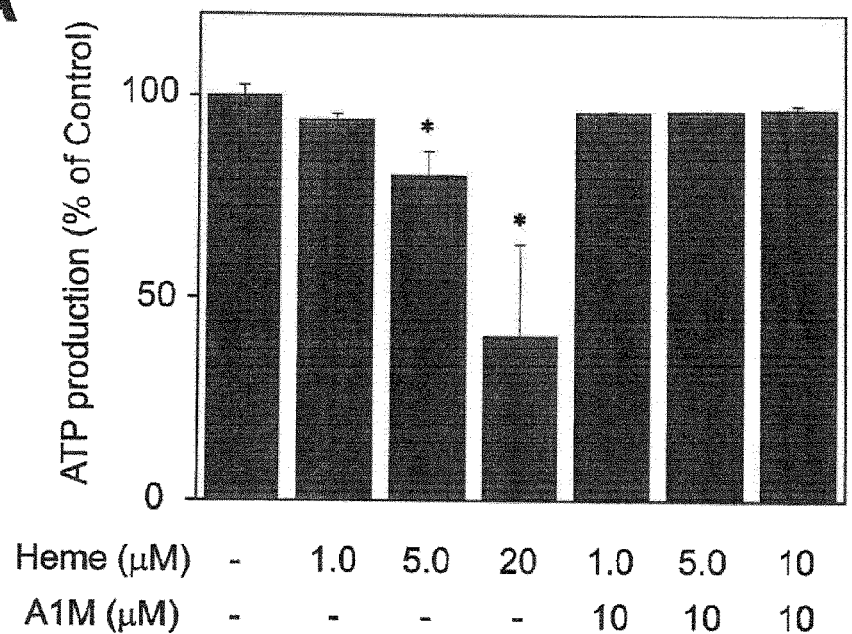
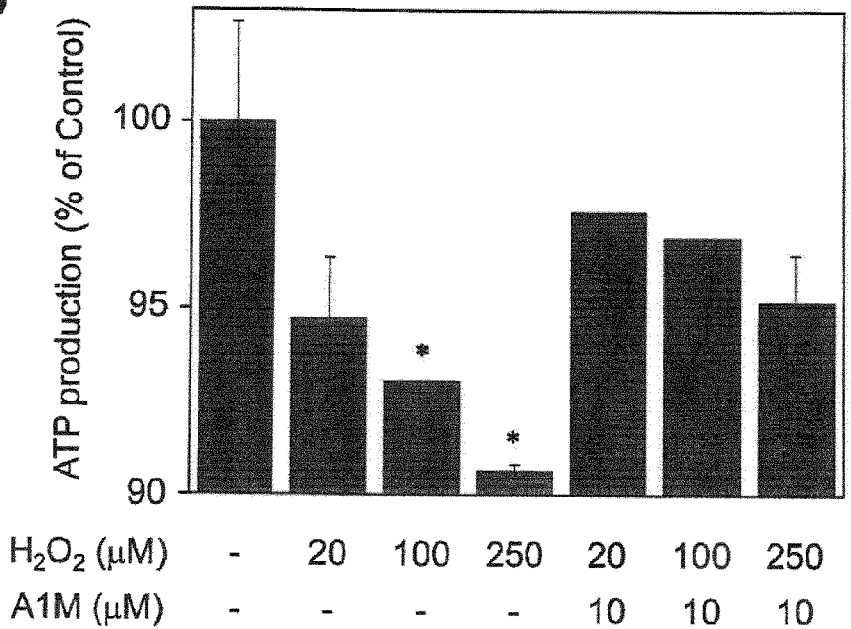
Figure 8

120912 A1M Sequence list_ST25.txt
SEQUENCE LISTING

<110> Akerstrm, Bo et al

<120> Alpha 1- microgobuin fr use in the treatment of mitochondria-related diseases
       1-microglobulin

<130> P81204108DK00

<160> 5

<170> PatentIn version 3.5

<210> 1
<211> 183
<212> PRT
<213> Homo sapiens

<400> 1

```
Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180
```

Figure 9

120912 AIM Sequence list_ST25.txt

<210> 2
<211> 201
<212> PRT
<213> Homo sapiens

<400> 2

Met His His His His His His Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
        35                  40                  45

Gly Ser Thr Cys Pro Trp Leu Lys Lys Ile Met Asp Arg Met Thr Val
    50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
        115                 120                 125

Tyr Ala Ile Phe Leu Thr Lys Lys Phe Ser Arg His His Gly Pro Thr
    130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
        195                 200

<210> 3
<211> 549
<212> DNA
<213> Homo sapiens

<400> 3
ggccctgtgc caacgccgcc cgacaacatc caagtgcagg aaaacttcaa tatctctcgg        60

Figure 9 (Continued)

120912 AIM Sequence list_ST25.txt

```
atctatggga agtggtacaa cctggccatc ggttccacct gccctggct gaagaagatc      120
atggacagga tgacagtgag cacgctggtg ctgggagagg gcgctacaga ggcggagatc      180
agcatgacca gcactcgttg gcggaaaggt gtctgtgagg agacgtctgg agcttatgag      240
aaaacagata ctgatgggag gtttctctat cacaaatcca aatggaacat aaccatggag      300
tcctatgtgg tccacaccac ctatgatgag tatgccattt ttctgaccaa gaaattcagc      360
cgccatcatg gaccaccat tactgccaag ctctacgggc gggcgcgca gctgagggaa        420
actctcctgc aggacttcag agtggttgcc cagggtgtgg gcatccctga ggactccatc      480
ttcaccatgg ctgaccgagg tgaatgtgtc cctggggagc aggaaccaga gcccatctta      540
atcccgaga                                                              549

<210> 4
<211> 603
<212> DNA
<213> Homo sapiens

<400> 4
atgcatcacc atcaccatca ccatcacggt ggaggagggg gtatcgaggg ccgcggccct      60
gtgccaacgc cgcccgacaa catccaagtg caggaaaact tcaatatctc tcggatctat      120
gggaagtggt acaacctggc catcggttcc acctgcccct ggctgaagaa gatcatggac      180
aggatgacag tgagcacgct ggtgctggga gaggcgcta cagaggcgga gatcagcatg      240
accagcactc gttggcggaa aggtgtctgt gaggagacgt ctggagctta tgagaaaaca      300
gatactgatg ggaggtttct ctatcacaaa tccaaatgga acataaccat ggagtcctat      360
gtggtccaca ccacctatga tgagtatgcc atttttctga ccaagaaatt cagccgccat      420
catggaccca ccattactgc caagctctac ggcggcgc cgcagctgag ggaaactctc        480
ctgcaggact tcagagtggt tgcccagggt gtgggcatcc ctgaggactc catcttcacc      540
atggctgacc gaggtgaatg tgtccctggg gagcaggaac cagagcccat cttaatcccg      600
aga                                                                    603

<210> 5
<211> 19
<212> RNA
<213> Artificial Sequence

<220>
<223> for silencing expression of alpha-1-microglobulin

<400> 5
ccuauguggu ccacaccaa                                                    19
```

Figure 9 (Continued)

ALPHA-1-MICROGLOBULIN FOR USE IN THE TREATMENT OF MITOCHONDRIA-RELATED DISEASES

SEQUENCE LISTING

The instant application contains a Sequence Listing which has been submitted electronically in ASCII format and is hereby incorporated by reference in its entirety. Said ASCII copy, created on Sep. 9, 2015, is named 105454-0105_SL.txt and is 6,353 bytes in size.

FIELD OF THE INVENTION

The present invention is based on the finding that alpha-1-microgobulin (A1M) plays an important role in protecting the mitochondria against damage. A1M binds to a Complex I subunit, thereby protecting the structure and function of the mitochondria. Mitochondria have been implicated in several human diseases and the findings disclosed herein support the use of A1M in the treatment of mitochondria-related diseases.

BACKGROUND OF THE INVENTION

Mitochondria are organelles in eukaryotic cells. They generate most of the cells' supply of adenosine triphosphate (ATP), which is used as an energy source. Thus, mitochondria are indispensable for energy production, for the survival of eukaryotic cells and for correct cellular function. In addition to supplying energy, mitochondria are involved in a number of other processes such as cell signaling, cellular differentiation, cell death as well as the control of the cell cycle and cell growth. In particular, mitochondria are crucial regulators of cell apoptosis and they also play a major role in multiple forms of non-apoptotic cell death such as, e.g., necrosis.

In recent years many papers have been published describing mitochondrial contribution to a variety of diseases. Some diseases may be caused by mutations or deletions in the mitochondrial genome, while others may be caused by damage of the mitochondrial function. At present there is treatment available that can cure mitochondrial diseases.

In view of the recognized importance of maintaining or restoring a normal mitochondrial function, there is a need to identify substances which can be used to protect the mitochondrial structure and function or which can be used to restore or treat dysfunctions in the mitochondria.

Alpha-1-microglobulin (A1M) is a 26 kDa plasma and tissue protein which has been isolated and characterized from plasma, liver and urine from several species including man and plaice (31). In plasma, A1M is found in free form as well as covalently bound to other larger plasma proteins. In humans, A1M forms complexes with IgA, albumin and prothrombin (5). Free A1M and various high-molecular weight complexes are also present in the extracellular matrix of all tissues both originating from plasma as well as from peripheral synthesis (4). In the tissues, A1M is preferentially localized to the interfaces between blood and tissue in blood vessels, air and tissue in the lung, and mother and fetus in placenta, especially at sites of injury (44). The physiological function of A1M is not known, but it has been shown to have reductase activity, and to bind free heme and radicals, suggesting that it may have protective functions during situations with oxidative stress (31). A1M binds to many cell types, in many instances followed by internalization (36, 49).

DETAILED DESCRIPTION OF THE INVENTION

The present inventors have made a detailed investigation of the cell uptake of A1M, and in the course of this it was found that the protein is mainly localized to mitochondria in damaged cells, and could protect mitochondrial structure and function.

The present invention relates to the use of A1M to prevent or treat mitochondria-related diseases. As shown in the examples, A1M has a beneficial effect on cells exposed to excessive amount of stress and forced to produce ATP at high rates. In such situations, A1M is capable of maintaining the ATP production of the cells in spite of environmental stress. As A1M binds to a subunit of the complexes of the respiratory chain, it is envisages that A1M generally can be used to prevent or treat diseases which involves impairment or damage of the mitochondria or damage of (at least parts of) the mitochondrial function.

Mitochondrial diseases result from failures of the mitochondria, which are specialized compartments present in every cell of the body except red blood cells. When mitochondria fail, less and less energy is generated within the cell and cell injury or even cell death will follow. If this process is repeated throughout the body the life of the person to whom this is happening is severely compromised.

Diseases of the mitochondria appear most often in organs that are very energy demanding such as the brain, heart, liver, skeletal muscles, kidney and the endocrine and respiratory system.

Symptoms of a mitochondrial disease may include loss of motor control, muscle weakness and pain, seizures, visual/hearing problems, cardiac diseases, liver diseases, gastrointestinal disorders, swallowing difficulties and more.

A mitochondrial disease may be inherited or may be due to spontaneous mutations, which lead to altered functions of the proteins or RNA molecules normally residing in the mitochondria.

Many diseases have been found to involve a mitochondrial deficiency such as a Complex I, II, III or IV deficiency or an enzyme deficiency like e.g. pyruvate dehydrogenase deficiency. However, the picture is complex and many factors may be involved in the diseases.

Up to now, no curative treatments are available. The only treatments available are such that can alleviate the symptoms and delay the progression of the disease.

Accordingly, the findings by the present inventors and described herein are very important as they demonstrate the beneficial effect of A1M on mitochondria both with respect to maintaining the mitochondrial structure and to the ability to restore an induced mitochondrial defect.

The invention relates to A1M for use in the treatment of a mitochondrial disease. Such diseases include—but are not limited to—diseases in the neurological system, the brain, heart, liver, skeletal muscles, kidney and the endocrine and respiratory system. Many diseases may have a mitochondrial defect and accordingly, more diseases than those mentioned herein may also be relevant to treat or prevent using A1M.

Cell death, whether accidental, stress-induced, or apoptotic, frequently involves activation of cell degradation and recycling programs (7). Therefore, cell death is an energy-depending process in need of preserved and intact mitochondrial functions. Autophagocytic elimination of mitochondria (mitophagy) is suggested to play a central role during programmed cell death (23). Thus, there is a need of functional mitochondria during programmed cell death, and it is not yet understood how this is accomplished.

Complex I, II, III and IV are protein complexes embedded in the inner membrane of the mitochondrion. They are known as the respiratory chain and function by coupling electron transfer between an electron donor (such as NADH) and an electron acceptor (such as $O_2$) with the transfer of $H^+$ ions. The resulting electrochemical proton gradient over the inner membrane is used to generate chemical energy in the form of adenosine triphosphate (ATP) by oxidation of glucose, pyruvate and NADH, which all are produced in the cytosol of the cell. This process of cellular respiration, also known as aerobic respiration, is dependent on the presence of oxygen. When oxygen is limited, the glycolytic products will be metabolized by anaerobic fermentation, a process that is independent of the mitochondria. The production of ATP from glucose is about 13 times higher during aerobic respiration compared to fermentation.

The present inventors have shown that the human plasma and tissue low molecular weight protein A1M binds to mitochondria and more specifically to mitochondrial Complex I. Furthermore, it was shown that the protein can protect mitochondria from heme-induced swelling and loss of ATP-production capacity. On the basis of these findings, we suggest that A1M may participate in the cell house-keeping mechanism. A1M may exert this protection by a number of different mechanisms, which are currently not known. Irrespective of the mechanism of action, the studies reported herein clearly indicate that A1M has beneficial effects to mitochondria and, accordingly, A1M is a potential drug substance for the treatment or prevention of mitochondrial diseases. Moreover, A1M may be used for the prevention and/or treatment of mitochondrial side effects in patients subject to treatment with drugs that cause such side effects. Examples include treatment with statins etc. Furthermore, A1M may be used in cosmetics, e.g. for treating age-related modifications of the skin, or it may be used in the prevention and/or treatment of unwanted mitochondrial effects caused by substances or conditions in our environment.

As mentioned above, A1M binds to a subunit of Complex I. This could indicate that A1M is especially suitable to use in the treatment of mitochondrial diseases where there is a defect in the respiratory chain. More specifically, it could indicate that A1M is especially suitable to use in the treatment of Complex I deficiency or Complex I related diseases.

As reported in the examples herein, induction of cell apoptosis was used to mimic situations characterized by stress-induced cell insults causing damage to the plasma membrane and destruction of the external barrier of the cell. Exogenous A1M was bound intracellularly with high affinity as soon as the cells could internalize propidium iodide (PI), suggesting that the uptake mechanism is a passive leakage of A1M from the extracellular compartment. Thus, binding of A1M to the mitochondria should also occur in necrotic cells with ruptured plasma membranes. It is becoming increasingly clear that many forms of in vivo necrotic cell-death actually can be described as a regulated series of ATP-dependent cell-disintegration events, i.e. programmed necrosis following specific pathways called necroptosis (7,46). Thus, a possible role for A1M is to participate in preservation of mitochondrial function in both apoptotic and necroptotic cells and possibly other types of necrotic cells during non-autophagic cell death, in order to ascertain availability of ATP for energy-dependent cell-degradation processes.

The mechanism of protection of mitochondrial structure and function is not known. A1M has been ascribed an antioxidant function based on its reductase, and heme- and radical-binding properties (2, 53). Therefore, it may be speculated that these properties are involved in the protective effects. Alternatively, since A1M seems to be an endogenous component of at least one of the large protein complexes (Complex I) it may have a structurally stabilizing effect on the complex. During apoptosis, necroptosis and other forms of cell death, additional binding of exogenous A1M may be necessary to maintain physicochemical structure and function of the respiratory protein complex. Another possibility is that the binding of A1M to Complex I may have beneficial effects on other components of the mitochondrial inner membrane, such as pore proteins or membrane lipids.

The interactions between A1M and mitochondria were investigated and specific binding was observed in several different cell types, i.e. human blood cells of lymphocytic, myelocytic and leukocyte origin, human keratinocytes, and isolated mouse liver mitochondria. Taken together, our results suggest that the interactions and protective effects studied here can be generalized to all types of cells.

As reported herein, A1M was found to interact with four different proteins: The NDUFAB1-subunit in the hydrophobic portion of the NADH dehydrogenase complex (45), N-acetylglucosamine kinase (18), the snRNA binding protein LSm5 (40), and a cancer antigen, NY-CO-3 (42). None of the four proteins was a false positive, i.e. interacting with the DNA-binding bait fusion protein or with any protein fused to it. Thus, the candidates were regarded as true A1M-interacting proteins in the yeast two-hybrid system. Considering that eight of the eleven clones isolated by the yeast two-hybrid system were the same Complex I-subunit, this protein was seen as the most interesting of the proteins and was therefore chosen as a target of further investigations. The binding to mitochondria also was supported by alternative methodological approaches and a functional role of the association could be ascribed as compatible with the antioxidation function of A1M. The physiological implications of the binding of A1M to N-acetylglucosamine kinase, the snRNA binding protein LSm5, and NY-CO-3 may be speculated upon, however. These proteins are located to the cytosol, nucleus, and plasma membrane, respectively, and the role of the binding to these proteins may be to localize internalized A1M to other cell-compartments besides mitochondria. Another possibility is that the binding to these three proteins reflect other functions of A1M unrelated to antioxidation and radical scavenging.

A1M is a member of the Lipocalin protein family. The lipocalins constitute a functionally diverse group of approximately 50 proteins from bacteria, plants and animals, having an amino acid sequence similarity usually around 20-25% and share certain structural common features that indicate a common evolutionary origin (11,12,51). Interestingly, two lipocalins found in plants and green algae, violaxanthin-deepoxidase (VDE) and zeaxanthin epoxidase (ZDE), are localized in the thylakoid membranes of chloroplasts, the ATP-producing photosynthetic organelle of plants, where they are associated with the light-harvesting system II and participate in the xanthophyll photoprotection system (reviewed in (14)). There is an obvious parallel between the violaxanthin protection cycle and the results in this paper: the presence of a lipocalin-based protection system in the energy-converting organelles of both plants and animals. Hypothesizing that mitochondria and chloroplasts have a common prokaryotic or eukaryotic ancestor (c.f. (15,30, 50)), one may speculate that these two lipocalin systems are evolutionarily related.

When a cell is subjected to a fatal insult it will ultimately be degraded and its components recycled. This is usually a highly complex and energy-consuming process that needs to be thoroughly controlled in order to protect the surrounding environment, i.e. neighboring cells and tissue, from further damage. Preservation and maintenance of the mitochondrial energy machinery during this process is vital. We show that the plasma and tissue glycoprotein A1M may have a central role in maintaining mitochondrial energy production and simultaneously assist the respiratory chain and thereby prevent unwanted, destructive reactions with healthy tissue. Thus, these findings suggest a novel mechanism of maintaining mitochondrial homeostasis.

In the present context the term "alpha-1-microglobulin" intends to cover alpha-1-microglobulin as identified in SEQ ID NO: 1 (human A1M) as well as SEQ ID NO: 2 (human recombinant A1M) as well as homologues, fragments or variants thereof having similar therapeutic activities. In a preferred aspect, the alpha-1-microglobulin is in accordance with SEQ ID NO: 1 or 2 as identified herein. In the sequence listing is given the sequence listing of the amino acid sequence of human A1M and human recombinant A1M (SEQ ID NOs 1 and 2, respectively) and the corresponding nucleotide sequences (SEQ ID NOs 3 and 4, respectively).

As mentioned above homologues of A1M can also be used in accordance with the description herein. In theory A1M from all species can be used including the most primitive found so far, which is from fish (plaice). A1M is also available in isolated form from human, rat, mouse, rabbit, guinea pig, cow and plaice.

Considering homologues, variants and fragments of A1M the following has been identified as important parts of the protein:
Y22 (Tyrosine, pos 22, basepairs 64-66)
C34 (Cystein, position 34, basepairs 100-102)
K69 (Lysine, pos 69, basepairs 205-207)
K92 (Lysine, pos 92, basepairs 274-276)
K118 (Lysine, pos 118, basepairs 352-354)
K130 (Lysine, pos 130, basepairs 388-390)
Y132 (Tyrosine, pos 132, basepairs 394-396)
L180 (Leucine, pos 180, basepairs 538-540)
I181 (Isoleucine, pos 181, basepairs 541-543)
P182 (Proline, pos 182, basepairs 544-546)
R183 (Arginine, pos 183, basepairs 547-549)
(Numbering of amino acids and nucleotides throughout the document refers to SEQ ID 1 and 3; if other A1M from other species, A1M analogs or recombinant sequences thereof are employed, a person skilled in the art will know how to identify the amino acids of the active site(s) or site(s) responsible for the enzymatic activity.)

In particular it has been observed that the cell protective effect of A1M is dependent on the free thiolyl group of the C34 side-chain and regulated by the K92, K118 and K130 residues. Thus, analogues of A1M containing these parts of the protein and/or configured in a similar way are believed to have similar effects as A1M and thus, encompassed by the present invention.

Human A1M is substituted with oligosaccharides in three positions, two sialylated complex-type, probably diantennary carbohydrated linked to Asn17 and Asn96 and one more simple oligosaccharide linked to Thr5. The carbohydrate content of A1M proteins from different species varies greatly, though, ranging from no glycosylation at all in *Xenopus leavis* over a spectrum of different glycosylation patterns. However, one glycosylation site, corresponding to Asn96 in man, is conserved in mammals, suggesting that this specific carbohydrate may be functionally important.

A1M is yellow-brown-coloured when purified from plasma or urine. The colour is caused by heterogeneous compounds covalently bound to various amino acid side groups mainly located at the entrance to the pocket. These modifications probably represent the oxidized degradation products of organic oxidants covalently trapped by A1M in vivo, for example heme, kynurenin and tyrosyl radicals.

A1M is also charge- and size-heterogeneous and more highly brown-coloured A1M-molecules are more negatively charged. The probable explanation for the heterogeneity is that different side-groups are modified to a varying degree with different radicals, and that the modifications alter the net charge of the protein. Covalently linked coloured substances have been localized to Cys34, and Lys92, Lys118 and Lys130, the latter with molecular masses between 100 and 300 Da. The tryptophan metabolite kynurenine was found covalently attached to lysyl residues in A1M from urine of haemodialysis patients and appears to be the source of the brown colour of the protein in this case. Oxidized fragments of the synthetic radical ABTS (2,2'-azino-di-(3-ethylbenzothiazoline)-6-sulfonic acid) was bound to the side-chains of Y22 and Y132.

C34 is the reactive centre of A1M. It becomes very electronegative, meaning that it has a high potential to give away electrons, by the proximity of the positively charged side-chains of K69, K92, K118 and K130, which induce a deprotonization of the C34 thiol group. Preliminary data shows that C34 is one of the most electronegative groups known.

Theoretically, the amino acids that characterize the unique enzymatic and non-enzymatic properties of A1M (C34, Y22, K92, K118, K130, Y132, L180, I181, P182, R183), which will be described in more detail below, can be arranged in a similar three-dimensional configuration on another framework, for instance a protein with the same global folding (another lipocalin) or a completely artificial organic or inorganic molecule such as a plastic polymer, a nanoparticle or metal polymer.

Accordingly, homologues, fragments or variants comprising a structure including the reactive centre and its surroundings as depicted above are preferred.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3);

proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred. Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids the hydrophilicity values of which are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Lle, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

In the present context, the homology between two amino acid sequences or between two nucleic acid sequences is described by the parameter "identity". Alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6.

Multiple alignments of protein sequences may be made using "ClustalW". Multiple alignments of DNA sequences may be done using the protein alignment as a template, replacing the amino acids with the corresponding codon from the DNA sequence.

Alternatively different software can be used for aligning amino acid sequences and DNA sequences. The alignment of two amino acid sequences is e.g. determined by using the Needle program from the EMBOSS package version 2.8.0. The Needle program implements the global alignment algorithm described in. The substitution matrix used is BLOSUM62, gap opening penalty is 10, and gap extension penalty is 0.5.

The degree of identity between an amino acid sequence; e.g. SEQ ID NO: 1 and a different amino acid sequence (e.g. SEQ ID NO: 2) is calculated as the number of exact matches in an alignment of the two sequences, divided by the length of the "SEQ ID NO: 1" or the length of the "SEQ ID NO: 2", whichever is the shortest. The result is expressed in percent identity.

An exact match occurs when the two sequences have identical amino acid residues in the same positions of the overlap.

If relevant, the degree of identity between two nucleotide sequences can be determined by the Wilbur-Lipman method using the LASER-GENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20. In a particular embodiment, the percentage of identity of an amino acid sequence of a polypeptide with, or to, amino acids of SEQ ID NO: 1 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage. The percentage of identity to, or with, other sequences of the invention is calculated in an analogous way.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence.

Figure 6:
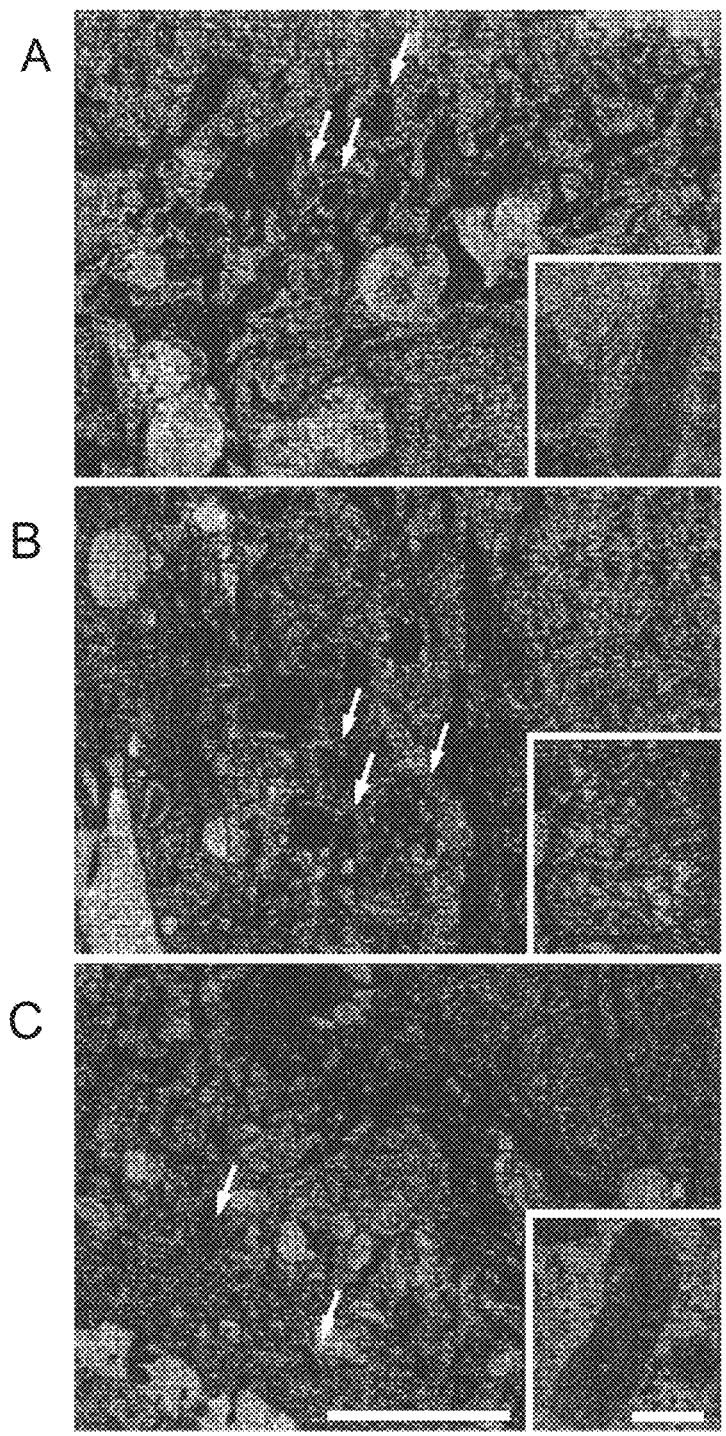

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylpróline, 3,3-dimethylproline, tert-leucine, norvaline, 2-azaphenyl-alanine, 3-azaphenylalanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. In a second method, translation is carried out in *Xenopus oocytes* by microinjection of mutated mRNA and chemically aminoacylated suppressor tRNAs. Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. Naturally occurring amino acid residues can be converted to non-naturally occurring species by in vitro chemical modification. Chemical modification can be combined with site-directed mutagenesis to further expand the range of substitutions. Alternative chemical structures providing a 3-dimensional structure sufficient to support the antioxidative properties of A1M may be provided by other technologies e.g. artificial scaffolds, amino-acid substitutions and the like. Furthermore, structures mimicking the active sites of A1M as listed above and depicted in FIGS. 3 and 6 are contemplated as having the same function as A1M.

A1M for Use in Specific Mitochondria-Related Diseases

More specifically, the invention relates to A1M for use in the treatment of a mitochondria-related disease selected from the following:

Alpers Disease (Progressive Infantile Poliodystrophy)
Barth syndrome (Lethal Infantile Cardiomyopathy)
Beta-oxidation Defects
Cardiomyopathy
Carnitine-Acyl-Carnitine Deficiency
Carnitine Deficiency
Creatine Deficiency Syndromes (Cerebral Creatine Deficiency Syndromes (CCDS) includes: Guanidinoaceteate Methyltransferase Deficiency (GAMT Deficiency), L-Arginine:Glycine Amidinotransferase Deficiency (AGAT Deficiency), and SLC6A8-Related Creatine Transporter Deficiency (SLC6A8 Deficiency).
Co-Enzyme Q10 Deficiency
Complex I Deficiency (NADH dehydrogenase (NADH-CoQ reductase) deficiency)
Complex II Deficiency (Succinate dehydrogenase deficiency)
Complex III Deficiency (Ubiquinone-cytochrome c oxidoreductase deficiency)
Complex IV Deficiency/COX Deficiency (Cytochrome c oxidase deficiency is caused by a defect in Complex IV of the respiratory chain)
Complex V Deficiency (ATP synthase deficiency)
COX Deficiency
CPEO (Chronic Progressive External Ophthalmoplegia Syndrome)
CPT I Deficiency
CPT II Deficiency
Friedreich's ataxia (FRDA or FA)
Encephalomyopathy
Glutaric Aciduria Type II
KSS (Kearns-Sayre Syndrome)
Lactic Acidosis
LCAD (Long-Chain Acyl-CoA Dehydrongenase Deficiency)
LCHAD
Leigh Disease or Syndrome (Subacute Necrotizing Encephalomyelopathy)
LHON (Leber's hereditary optic neuropathy)
Luft Disease
MCAD (Medium-Chain Acyl-CoA Dehydrongenase Deficiency)
MELAS (Mitochondrial Encephalomyopathy Lactic Acidosis and Stroke-like Episodes)
MERRF (Myoclonic Epilepsy and Ragged-Red Fiber Disease)
MIRAS (Mitochondrial Recessive Ataxia Syndrome)
Mitochondrial Cytopathy
Mitochondrial DNA Depletion
Mitochondrial Encephalopathy includes: Encephalomyopathy, Encephalomyelopathy
Mitochondrial Myopathy
MNGIE (Myoneurogastointestinal Disorder and Encephalopathy)
NARP (Neuropathy, Ataxia, and Retinitis Pigmentosa)
Pearson Syndrome
Pyruvate Carboxylase Deficiency
Pyruvate Dehydrogenase Deficiency
POLG Mutations
Respiratory Chain Deficiencies
SCAD (Short-Chain Acyl-CoA Dehydrogenase Deficiency)
SCHAD
VLCAD (Very Long-Chain Acyl-CoA Dehydrongenase Deficiency)

With reference to information from the web-page of United Mitochondrial Disease Foundation, some of the above-mentioned diseases are discussed in more details in the following:

Complex 1 Deficiency:

Inside the mitochondrion is a group of proteins that carry electrons along four chain reactions (Complexes I-IV), resulting in energy production. This chain is known as the Electron Transport Chain. A fifth group (Complex V) churns out the ATP. Together, the electron transport chain and the ATP synthase form the respiratory chain and the whole process is known as oxidative phosphorylation or OXPHOS.

Complex I, the first step in this chain, is the most common site for mitochondrial abnormalities, representing as much as one third of the respiratory chain deficiencies. Often presenting at birth or in early childhood, Complex I deficiency is usually a progressive neuro-degenerative disorder and is responsible for a variety of clinical symptoms, particularly in organs and tissues that require high energy levels, such as brain, heart, liver, and skeletal muscles. A number of specific mitochondrial disorders have been associated with Complex I deficiency including: Leber's hereditary optic neuropathy (LHON), MELAS, MERRF, and Leigh Syndrome (LS).

There are three major forms of Complex I deficiency:

i) Fatal infantile multisystem disorder—characterized by poor muscle tone, developmental delay, heart disease, lactic acidosis, and respiratory failure.

ii) Myopathy (muscle disease)—starting in childhood or adulthood, and characterized by weakness or exercise intolerance.

iii) Mitochondrial encephalomyopathy (brain and muscle disease)—beginning in childhood or adulthood and involving variable symptom combinations which may include: eye muscle paralysis, pigmentary retinopathy (retinal colour changes with loss of vision), hearing loss, sensory neuropathy (nerve damage involving the sense organs), seizures, dementia, ataxia (abnormal muscle coordination), and involuntary movements. This form of Complex I deficiency may cause Leigh Syndrome and MELAS.

Most cases of Complex I deficiency result from autosomal recessive inheritance (combination of defective nuclear genes from both the mother and the father). Less frequently, the disorder is maternally inherited or sporadic and the genetic defect is in the mitochondrial DNA.

Treatment: As with all mitochondrial diseases, there is presently no cure for Complex I deficiency. A variety of treatments, which may or may not be effective, can include such metabolic therapies as: riboflavin, thiamine, biotin, co-enzyme Q10, carnitine, and the ketogenic diet. Therapies for the infantile multisystem form have been unsuccessful.

The clinical course and prognosis for Complex I patients is highly variable and may depend on the specific genetic defect, age of onset, organs involved, and other factors.

Complex III Deficiency:

The symptoms include four major forms:

i) Fatal infantile encephalomyopathy, congenital lactic acidosis, hypotonia, dystrophic posturing, seizures, and coma. Ragged-red fibres common.

ii) Encephalomyopathies of later onset (childhood to adult life): various combinations of weakness, short stature, ataxia, dementia, hearing loss, sensory neuropathy, pigmentary retinopathy, and pyramidal signs. Ragged-red fibres common. Possible lactic acidosis.

iii) Myopathy, with exercise intolerance evolving into fixed weakness. Ragged-red fibres common. Possible lactic acidosis.

iv) Infantile histiocytoid cardiomyopathy.

Complex IV Deficiency/COX Deficiency: The symptoms include two major forms:

1. Encephalomyopathy: Typically normal for the first 6 to 12 months of life and then show developmental regression, ataxia, lactic acidosis, optic atrophy, ophthalmoplegia, nystagmus, dystonia, pyramidal signs, and respiratory problems. Frequent seizures. May cause Leigh Syndrome
2. Myopathy: Two main variants:
   1. Fatal infantile myopathy: may begin soon after birth and accompanied by hypotonia, weakness, lactic acidosis, ragged-red fibres, respiratory failure, and kidney problems.
   2. Benign infantile myopathy: may begin soon after birth and accompanied by hypotonia, weakness, lactic acidosis, ragged-red fibres, respiratory problems, but (if the child survives) followed by spontaneous improvement.

KSS (Kearns-Sayre Syndrome): KSS is a slowly progressive multi-system mitochondrial disease that often begins with drooping of the eyelids (ptosis). Other eye muscles eventually become involved, resulting in paralysis of eye movement. Degeneration of the retina usually causes difficulty seeing in dimly lit environments.

KSS is characterized by three main features:
typical onset before age 20 although may occur in infancy or adulthood
paralysis of specific eye muscles (called chronic progressive external ophthalmoplegia—CPEO)
degeneration of the retina causing abnormal accumulation of pigmented (coloured)material (pigmentary retinopathy).

In addition, one or more of the following conditions is present:
block of electrical signals in the heart (cardiac conduction defects)
elevated cerebrospinal fluid protein
incoordination of movements (ataxia).

Patients with KSS may also have such problems as deafness, dementia, kidney dysfunction, and muscle weakness. Endocrine abnormalities including growth retardation, short stature, or diabetes may also be evident.

KSS is a rare disorder. It is usually caused by a single large deletion (loss) of genetic material within the DNA of the mitochondria (mtDNA), rather than in the DNA of the cell nucleus. These deletions, of which there are over 150 species, typically arise spontaneously. Less frequently, the mutation is transmitted by the mother.

As with all mitochondrial diseases, there is no cure for KSS.

Treatments are based on the types of symptoms and organs involved, and may include: Coenzyme Q10, insulin for diabetes, cardiac drugs, and a cardiac pacemaker which may be life-saving. Surgical intervention for drooping eyelids may be considered but should be undertaken by specialists in ophthalmic surgical centres.

KSS is slowly progressive and the prognosis varies depending on severity. Death is common in the third or fourth decade and may be due to organ system failures.

Leigh Disease or Syndrome (Subacute Necrotizing Encephalomyelopathy):

Symptoms: Seizures, hypotonia, fatigue, nystagmus, poor reflexes, eating & swallowing difficulties, breathing problems, poor motor function, and ataxia.

Causes: Pyruvate Dehydrogenase Deficiency, Complex I Deficiency, Complex II Deficiency, Complex IV/COX Deficiency, NARP.

Leigh's Disease is a progressive neurometabolic disorder with a general onset in infancy or childhood, often after a viral infection, but can also occur in teens and adults. It is characterized on MRI by visible necrotizing (dead or dying tissue) lesions on the brain, particularly in the midbrain and brainstem.

The child often appears normal at birth but typically begins displaying symptoms within a few months to two years of age, although the timing may be much earlier or later. Initial symptoms can include the loss of basic skills such as sucking, head control, walking and talking. These may be accompanied by other problems such as irritability, loss of appetite, vomiting and seizures. There may be periods of sharp decline or temporary restoration of some functions. Eventually, the child may also have heart, kidney, vision, and breathing complications.

There is more than one defect that causes Leigh's Disease. These include a pyruvate dehydrogenase (PDHC) deficiency, and respiratory chain enzyme defects—Complexes I, II, IV, and V. Depending on the defect, the mode of inheritance may be X-linked dominant (defect on the X chromosome and disease usually occurs in males only), autosomal recessive (inherited from genes from both mother and father), and maternal (from mother only). There may also be spontaneous cases which are not inherited at all.

There is no cure for Leigh's Disease. Treatments generally involve variations of vitamin and supplement therapies, often in a "cocktail" combination, and are only partially effective. Various resource sites include the possible usage of: thiamine, coenzyme Q10, riboflavin, biotin, creatine, succinate, and idebenone. Experimental drugs, such as dichloroacetate (DCA) are also being tried in some clinics. In some cases, a special diet may be ordered and must be monitored by a dietician knowledgeable in metabolic disorders.

The prognosis for Leigh's Disease is poor. Depending on the defect, individuals typically live anywhere from a few years to the mid-teens. Those diagnosed with Leigh-like syndrome or who did not display symptoms until adulthood tend to live longer.

MELAS (Mitochondrial Encephalomyopathy Lactic Acidosis and Stroke-Like Episodes):

Symptoms: Short statue, seizures, stroke-like episodes with focused neurological deficits, recurrent headaches, cognitive regression, disease progression, ragged-red fibres.

Cause: Mitochondrial DNA point mutations: A3243G (most common)

MELAS—Mitochondrial Myopathy (muscle weakness), Encephalopathy (brain and central nervous system disease), Lactic Acidosis (build-up of a cell waste product), and Stroke-like Episodes (partial paralysis, partial vision loss, or other neurological abnormalities)

MELAS is a progressive neurodegenerative disorder with typical onset between the ages of 2 and 15, although it may occur in infancy or as late as adulthood. Initial symptoms may include stroke-like episodes, seizures, migraine headaches, and recurrent vomiting.

Usually, the patient appears normal during infancy, although short stature is common. Less common are early infancy symptoms that may include developmental delay, learning disabilities or attention-deficit disorder. Exercise intolerance, limb weakness, hearing loss, and diabetes may also precede the occurrence of the stroke-like episodes.

Stroke-like episodes, often accompanied by seizures, are the hallmark symptom of MELAS and cause partial paralysis, loss of vision, and focal neurological defects. The gradual cumulative effects of these episodes often result in variable combinations of loss of motor skills (speech, movement, and eating), impaired sensation (vision loss and loss of body sensations), and mental impairment (dementia). MELAS patients may also suffer additional symptoms including: muscle weakness, peripheral nerve dysfunction, diabetes, hearing loss, cardiac and kidney problems, and digestive abnormalities. Lactic acid usually accumulates at high levels in the blood, cerebrospinal fluid, or both.

MELAS is maternally inherited due to a defect in the DNA within mitochondria. There are at least 17 different mutations that can cause MELAS. By far the most prevalent is the A3243G mutation, which is responsible for about 80% of the cases.

There is no cure or specific treatment for MELAS. Although clinical trials have not proven their efficacy, general treatments may include such metabolic therapies as: CoQ10, creatine, phylloquinone, and other vitamins and supplements. Drugs such as seizure medications and insulin may be required for additional symptom management. Some patients with muscle dysfunction may benefit from moderate supervised exercise. In select cases, other therapies that may be prescribed include dichloroacetate (DCA) and menadione, though these are not routinely used due to their potential for having harmful side effects.

The prognosis for MELAS is poor. Typically, the age of death is between 10 to 35 years, although some patients may live longer. Death may come as a result of general body wasting due to progressive dementia and muscle weakness, or complications from other affected organs such as heart or kidneys.

MERRF is a progressive multi-system syndrome usually beginning in childhood, but onset may occur in adulthood. The rate of progression varies widely. Onset and extent of symptoms can differ among affected siblings.

The classic features of MERRF include:
Myoclonus (brief, sudden, twitching muscle spasms)— the most characteristic symptom Epileptic seizures Ataxia (impaired coordination)

Ragged-red fibres (a characteristic microscopic abnormality observed in muscle biopsy of patients with MERRF and other mitochondrial disorders) Additional symptoms may include: hearing loss, lactic acidosis (elevated lactic acid level in the blood), short stature, exercise intolerance, dementia, cardiac defects, eye abnormalities, and speech impairment.

Although a few cases of MERRF are sporadic, most cases are maternally inherited due to a mutation within the mitochondria. The most common MERRF mutation is A8344G, which accounted for over 80% of the cases (GeneReview article). Four other mitochondrial DNA mutations have been reported to cause MERRF. While a mother will transmit her MERRF mutation to all of her offspring, some may never display symptoms.

As with all mitochondrial disorders, there is no cure for MERRF. Therapies may include coenzyme Q10, L-carnitine, and various vitamins, often in a "cocktail" combination. Management of seizures usually requires anticonvulsant drugs. Medications for control of other symptoms may also be necessary.

The prognosis for MERRF varies widely depending on age of onset, type and severity of symptoms, organs involved, and other factors.

Mitochondrial DNA Depletion:

The symptoms include three major forms:

1. Congenital myopathy: Neonatal weakness, hypotonia requiring assisted ventilation, possible renal dysfunction. Severe lactic acidosis. Prominent ragged-red fibres. Death due to respiratory failure usually occurs prior to one year of age.

2. Infantile myopathy: Following normal early development until one year old, weakness appears and worsens rapidly, causing respiratory failure and death typically within a few years.

3. Hepatopathy: Enlarged liver and intractable liver failure, myopathy. Severe lactic acidosis. Death is typical within the first year.

The invention relates to the use of alpha-1-microglobulin in in the treatment of a mitochondria-related disease. The disease may be anyone of the diseases specified herein either as the sole disease or in any combination of diseases specified herein, For instance the invention relates to the use of alpha-1-microglobulin in the treatment of one of the diseases mentioned herein or in the treatment of a selection of the diseases mentioned herein irrespective of whether the specific selection has been explicitly mentioned. Thus, the selection of diseases or disorders may be randomly selected. The disease may be or is caused by a mitochondria defect or irregularity in the mitochondrial function.

In particular the invention relates to the use of alpha-1-microglobulin in the treatment or prophylaxis of respiratory chain disorders. More specifically the respiratory chain disorders involve Complex I, II, III, IV or V defects.

More specific the invention relates to the use of alpha-1-microglobulin in the treatment or prophylaxis of mitochondrial dysfunctions in children or young adults. Examples include Alpers disease, Barth syndrome, Fridreich's ataxia, KSS, Leigh Disease or Syndrome, LHON, MELAS, MERRF, MIRAS and NARP More specific the invention relates to the use of alpha-1-microglobulin in the treatment or prophylaxis of mitochondrial dysfunctions in women.

The invention also relates to the use of alpha-1-microglobulin in the treatment or prophylaxis of damage or dysfunction of retina or ocular diseases associated with mitochondrial defect(s) or dysfunction(s).

Therapeutic Administration:

The route and/or mode of administration of A1M can vary depending on the desired result. A person skilled in the art is aware that routes or modes of administration, as well as regimens, can be adjusted to provide the desired therapeutic response. Routes of administration include, but are not limited to, parenteral, enteral, mucosal/topical administration including intravenous, subcutaneous, intramuscular, intradermal, intracerebral, oral, peroral, dermal, by inhalation etc.

A1M may be formulated into a pharmaceutical composition designed for the particular use. A person skilled in the art will know how to find guidance for designing various pharmaceutical compositions, see e.g. Remington's Pharmaceutical Sciences, 18 Ed. 1990, Mack Publishing.

For ocular administration A1M may be formulated in a liquid composition or in a medical device including contact lenses or other ophthalmic inserts. Liquid compositions include solutions, dispersions, emulsions and suspensions and may be presented in the form of eye-drops either in single-dose form or in multiple-dose form, or it may be presented as dry powders for reconstitution with a liquid before application. The composition may also be presented as eye lotions, creams, ointments or gels. Pharmaceutically acceptable excipients may be included such as solvents (e.g. water, oils including natural or vegetable oils like e.g. castor oil), a viscosity-increasing agent like gellan gum, xanthan gum, polyvinyl alcohols, cellulose derivatives e.g. sodium carboxymethylcellulose, methylcellulose etc.), preservatives like parabens or benzalkonium chloride, pH adjusting agents (e.g. hydrochloric acid, sodium hydroxide, buffers like phosphate or citrate), stability-increasing agents, tonicity adjusting agents (e.g. sodium chloride) etc.

For oral administration A1M may be formulated in solid, semi-solid or liquid compositions. The compositions may be in unit-dosage form or in multiple-unit dosage form. Compositions include powders, tablets, capsules, sachets, films, wafers, gels, creams, ointments, solutions, dispersions, emulsions, suspensions, sprays etc. The composition includes one of more pharmaceutically acceptable excipient. Such excipients (and excipients for other kinds of compositions) are well-known to a person skilled in the art (see e.g. "Remington's Pharmaceutical Science" edited by Gennaro et al. (Mack Publishing Company), in "Handbook of Pharmaceutical Excipients" edited by Rowe et al. (PhP Press) and in official Monographs (e.g. Ph.Eur. or USP) relating to relevant excipients for specific formulation types and to methods for preparing a specific formulation.

A1M is preferably administered in the form of a pharmaceutical composition. Due to the polypeptide nature of A1M the compositions may preferably be designed for parenteral use, but A1M may also be applied locally e.g. on the skin in connection with healing of wounds, in joints, or in the brain cavities. A1M can be formulated in a liquid, e.g. in a solution, a dispersion, an emulsion, a suspension etc., or it may be in a formulation suitable for administration to the skin such as, e.g., a lotion, a cream, an ointment, a suspension, an emulsion, a paste, a powder, a patch, a plaster, a dressing, a soap, a shampoo, sun protection lotion etc. Moreover, A1M may be included in medical devices or equipment, e.g. as a releasable coating on catheters etc.

Alternatively and in addition, specific carriers to target the active substance to a specific part of the body can be included. For example an antibody-A1M complex where the antibody is targeted to the locality of choice ("homing") by its specificity for a certain epitope; a stem cell or a recombinant cell with such homing properties, e.g. integrin-receptors specific for a tissue and with the artificial or natural capacity to secrete large amounts of A1M. The treatment would be more efficient since the drug would be concentrated to a particular site, bleeding, etc., and less A1M would be required.

For parenteral use suitable solvents include water, vegetable oils, propylene glycol and organic solvents generally approved for such purposes. In general, a person skilled in the art can find guidance in "Remington's Pharmaceutical Science" edited by Gennaro et al. (Mack Publishing Company), in "Handbook of Pharmaceutical Excipients" edited by Rowe et al. (PhP Press) and in official Monographs (e.g. Ph.Eur. or USP) relating to relevant excipients for specific formulation types and to methods for preparing a specific formulation.

The invention is illustrated in the following figures and examples.

LEGEND TO FIGURES

FIG. 1. Binding of A1M to intact and apoptotic cells. A. HCQ.4 cells were cultured on hamster anti-mouse CD3 antibody (4 µg/ml) coated plastics for 18 hours. For analysis of A1M binding, $1 \times 10^6$ cells were incubated with 1 mg/ml A1M, washed, incubated with mouse anti-A1M antibodies, washed and finally incubated with FITC-conjugated goat anti-mouse IgG (GAM-FITC). 10 000 cells were analyzed for A1M binding (open peak). Background was set by cells incubated with BSA in the first step (shaded peak). Binding to apoptotic cells (right histogram) was compared to untreated cells (left histogram). B. The binding of A1M was correlated to the uptake of PI by culturing HCQ.4 cells in the presence of 5% ethanol or 10% DMSO for 15 hours. For the flow cytometry analysis, A1M was incubated with cells, followed by mouse anti-A1M antibodies and FITC-conjugated goat anti-mouse IgG. Before analysis, cells were also stained by PI to detect dead cells. C. Binding of A1M to apoptotic cells of the pre-B-cell line 70Z/3 was analyzed by flow cytometry. The cells were induced to apoptosis by the benzamide drug declopramide (3-CPA) for 15 hours and analyzed for A1M binding by incubation of biotinylated A1M, followed by SAPE. The background was set by cells incubated with SAPE only (shaded peak). D. K562 cells incubated with 20 µM and 0.25 mg/ml A1M for 2 h and subjected to staining with mouse anti-A1M antibodies followed by goat anti-mouse IgG F(ab')$_2$-fragments (Alexa Fluor® 594; red). Cells were mounted using ProLong Gold AntiFade Reagent with DAPI and visual inspection and recording was performed. The picture is representative for three separate experiments. Sizebar is 10 µM. E. The specificity of the A1M binding was determined by a competitive cell-binding assay. HCQ.4 cells, induced to apoptosis by cross-linking with anti-CD3 for 18 hours (right histogram), were compared to untreated HCQ.4 cells (left histogram). $1 \times 10^6$ cells/sample were mixed with 1 µg/ml of $^{126}$I-A1M (1), $^{125}$I-A1M plus addition of 2.5 mg/ml of unlabeled A1M (2), ovalbumin (3), BSA (4) or AGP (5). The cells were incubated for 30 minutes at 4° C. centrifuged on a sucrose-gradient to separate unbound protein, tubes were then frozen and cell-pellet cut off and counted in a γ-counter. The results are presented as mean values of a triplicate from one experiment±SEM. Statistical comparison between groups was made using Student's t test. *** P<0.001.

Figure 2:
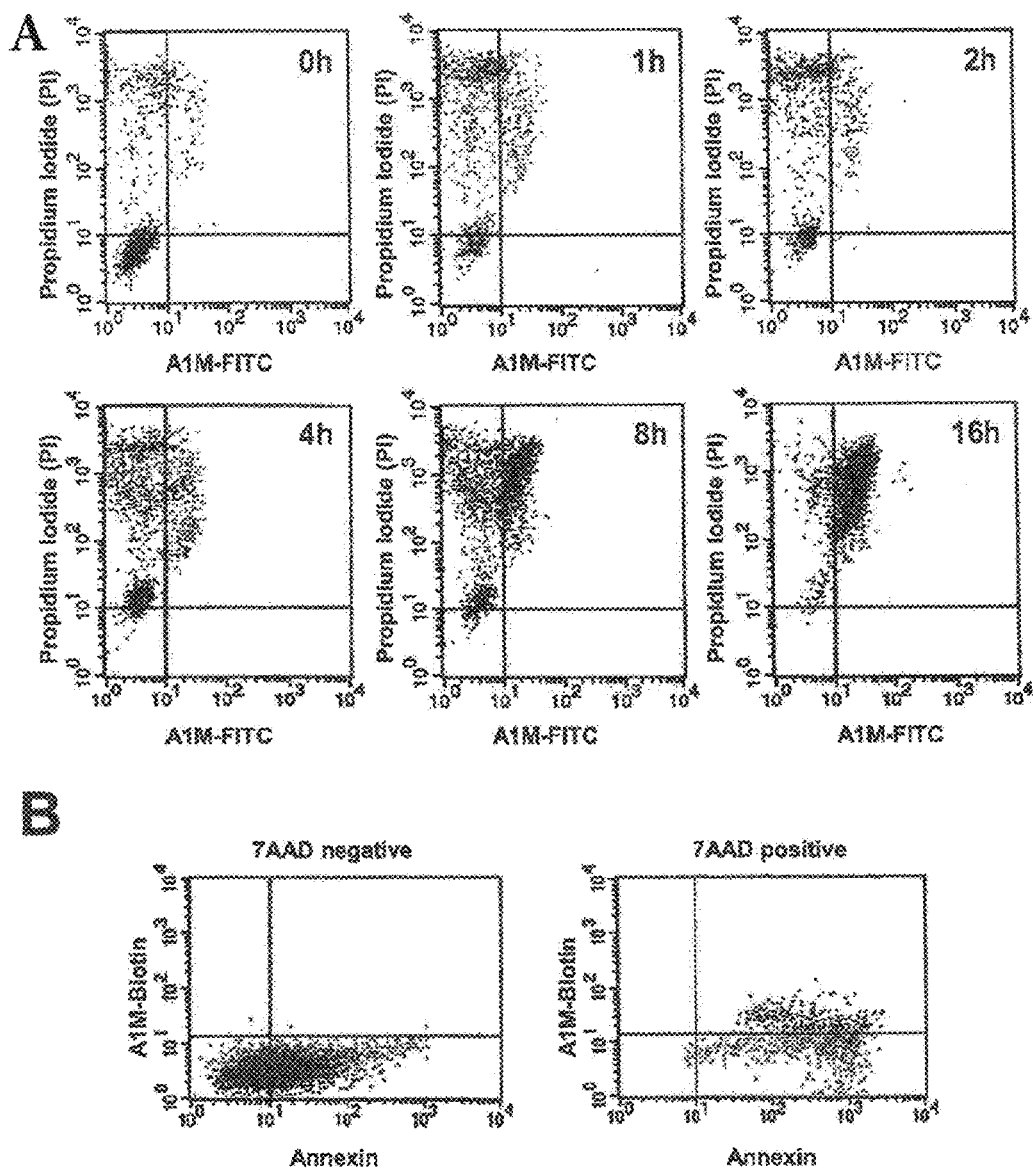

FIG. 2. Time-studies of the binding of A1M to apoptotic cells. A. Apoptosis was induced in HCQ.4 cells by cultivation on anti-CD3 coated plastics. Samples were taken at different time-points after induction (0, 1, 2, 4, 8 and 16 hours). The cells were stained with FITC-conjugated A1M (0.1 mg/ml) and PI. 10 000 cells were analyzed. B. Binding of A1M to pre-B-cells, induced to apoptosis by incubation with the benzamide 3-CPA, were analyzed by flow cytometry and correlated to binding of annexin V and 7AAD uptake. The apoptotic 70Z/3 cells were incubated with biotinylated A1M (0.025 mg/ml) followed by SAPE, annexin V and 7AAD. 10 000 cells were analyzed and gated for 7AAD negative (left diagram) and 7AAD positive cells (right diagram) respectively.

FIG. 3. Binding of A1M to mitochondria analyzed by confocal microscopy and transmission electron microscopy. A. K562 cells incubated with medium only (left) or 0.25 mg/ml A1M (right) for 2 h were washed and incubated with Mito-Tracker (red) for 15 minutes, and washed in fresh medium. After washing, cells were then stained with monoclonal mouse anti-A1M (BN 11.3) at 5 µg/ml followed by goat anti-mouse IgG F(ab')$_2$ fragments (Alexa Fluor® 488; green). Cells were mounted using ProLong Gold AntiFade Reagent with DAPI (blue) and visual inspection and recording was performed using confocal microscopy. The picture is representative of three separate experiments. Scale bar indicates 5 µm. B. An overview of human primary keratinocytes incubated for 20 hours at RT with 10 µM A1M. Mitochondrial structures are highlighted with arrows and shown in higher magnification in (C). Immunolabeling of human primary keratinocyte thin sections with gold-labeled anti-A1M was performed and shown to correlate to mitochondria. This is highlighted with arrowheads (C). The samples were prepared and observed as described in Materials and Methods. Scale bar in (B) indicates 2 µm and in (C) 0.1 µm.

Figure 4:
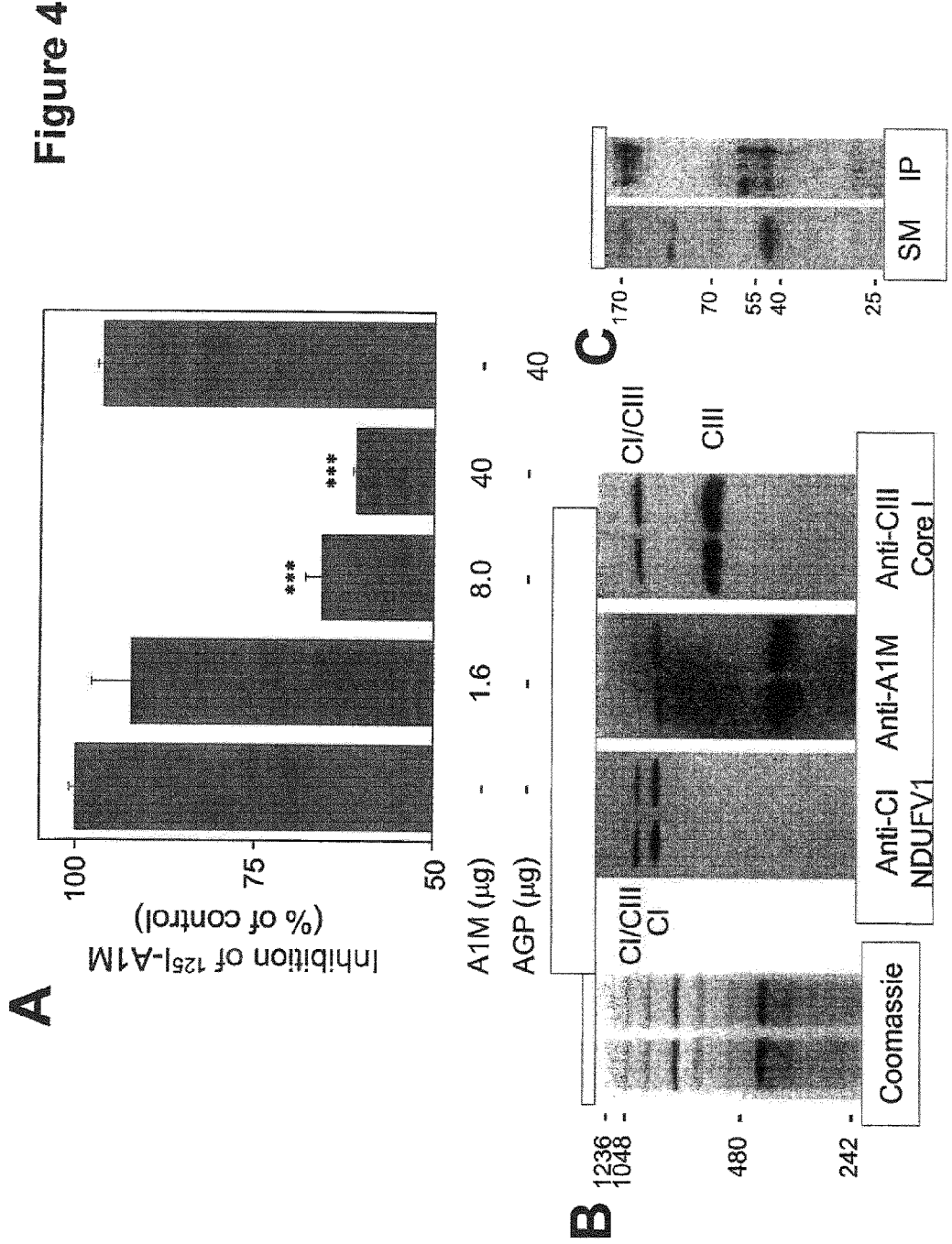

FIG. 4. Binding of A1M to mitochondria analyzed by $^{125}$I-A1M binding. A. The specificity of A1M-binding to mitochondria was investigated by mixing approximately 2.5 µg/ml of $^{125}$I-A1M with 0.5 mg purified mitochondria in the presence or absence of 1.0 mg/ml of unlabeled protein (A1M or AGP) in PBS+4% BSA. The mixtures were incubated at 4° C. for 30 minutes, centrifuged on a sucrose-gradient to separate unbound protein, tubes were then frozen and cell-pellet cut off and counted in a γ-counter. Each point represents the mean±SEM of three determinations. Statistical comparison between groups was made using Student's t test. ***P<0.001. B. The specificity of A1M-binding to mitochondria was further investigated using BN-PAGE and Western blotting. Five µg mitochondrial membrane proteins from 2 separate individuals were separated on a BN-PAGE 4-16% Bis-Tris gel and blotted to a PVDF membrane. After blocking, the membranes were incubated with antibodies against subunit NDUFV1 of Complex I, Core I of Complex III, mouse A1M, or stained with Coomassie. C. The Complex I association was also investigated by immunoprecipitation of freshly prepared mitochondria with antibodies against Complex I. Following the immunoprecipitation, bound and eluted proteins were separated on 12% SDS-PAGE and blotted to PVDF membrane. After blocking, the membranes were incubated with antibodies against mouse A1M. Left lane, mitochondrial starting material (SM) and right lane, bound and eluted material (IP).

Figure 5:
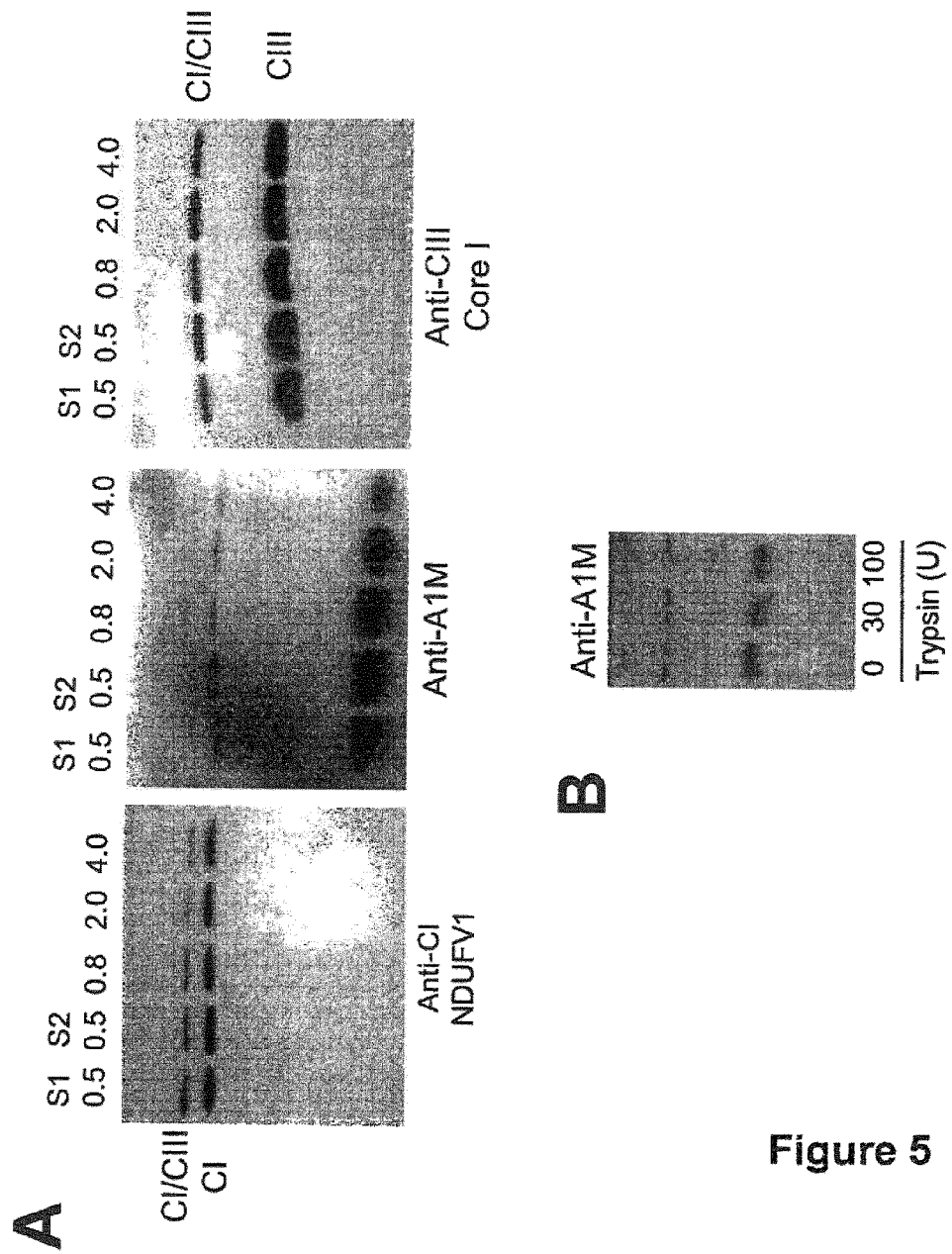

FIG. 5. The specificity of A1M-binding to mitochondria was investigated using BN-PAGE, SDS-PAGE and Western blotting. Freshly isolated mitochondria were suspended in PBS, pelleted by centrifugation and dissolved to a concentration of 5 mg/ml in MB2 buffer. Mitochondrial membrane proteins were solubilized by incubation with 0.5-4.0 g digitonin/g protein for 5 min on ice. Samples were centrifuged, the supernatant was collected and SBG was added to a final concentration of 4.5%. A. Five µg mitochondrial membrane proteins from 2 separate individuals (S1 and S2) were then separated on a BN-PAGE 4-16% Bis-Tris gel and blotted to a PVDF membrane. After blocking, the membranes were incubated with antibodies against subunit NDUFV1 (left) of Complex I, A1M (middle) and subunit Core I of Complex III. B. Trypsin treated (0-100 U Trypsin) isolated mitochondrial proteins (15 pg/lane) were separated on 12% SDS-PAGE and transferred to a PVDF membrane. After blocking, the membrane was incubated with antibodies against A1M.

FIG. 6. A1M protects mitochondrial structure. Human primary keratinocytes were incubated for 20 hours at RT with culture medium only (A), 20 µM heme (B) or 20 µM heme+0.25 mg/ml A1M (C). Mitochondrial structures are highlighted with arrows and depicted in details (zoomed pictures). The samples were prepared and observed as described in Materials and Methods. Scale bar indicates 2 µm (overview) and 0.5 µm (zoomed picture).

Figure 7:
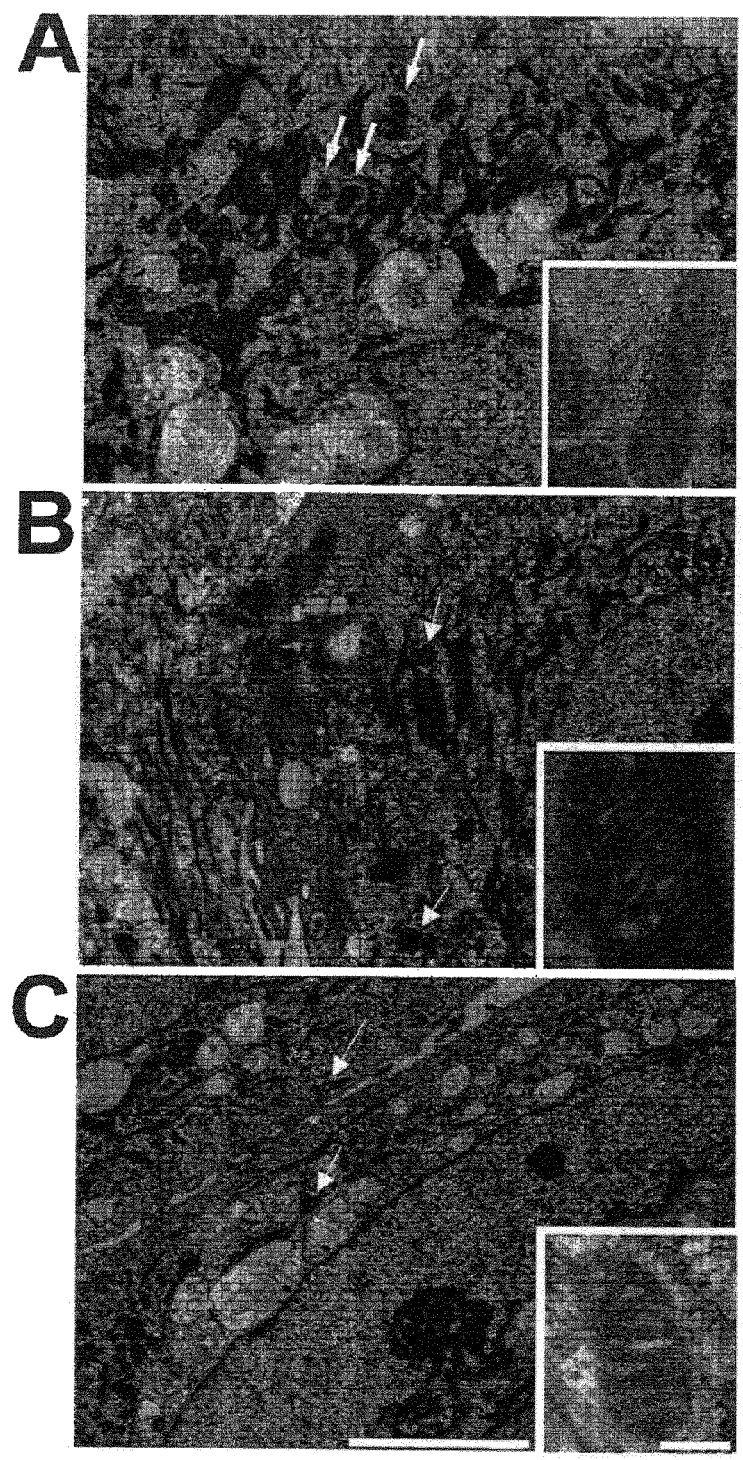

FIG. 7. Human primary keratinocytes were incubated for 20 hours at RT with culture medium only (A), 250 µM $H_2O_2$ (B) or 250 µM $H_2O_2$+0.25 mg/ml A1M (C). Mitochondrial structures are highlighted with arrows and depicted in details (zoomed pictures). The samples were prepared and observed as described in Materials and Methods. Scale bar indicates 2 µm (overview) and 0.5 µm (zoomed picture).

FIG. 8. A1M protects mitochondrial function. The effect of A1M on mitochondrial function was investigated by measuring ATP-production of purified mitochondria exposed to heme or $H_2O_2$. Mitochondria were incubated with 1-20 µM heme, with or without 0.25 mg/ml A1M (A) or 20-250 µM $H_2O_2$ with or without 0.25 mg/ml A1M (B) for 30 minutes. Mitochondria were collected by centrifugation and ATP-production was measured using a luminescence assay kit. ATP levels were normalized to the corresponding sample protein. Each point represents the mean±SEM of three determinations. Statistical comparison between groups was made using Student's t test. *P<0.05.

FIG. 9. Sequence listing of A1M

Figure 10:
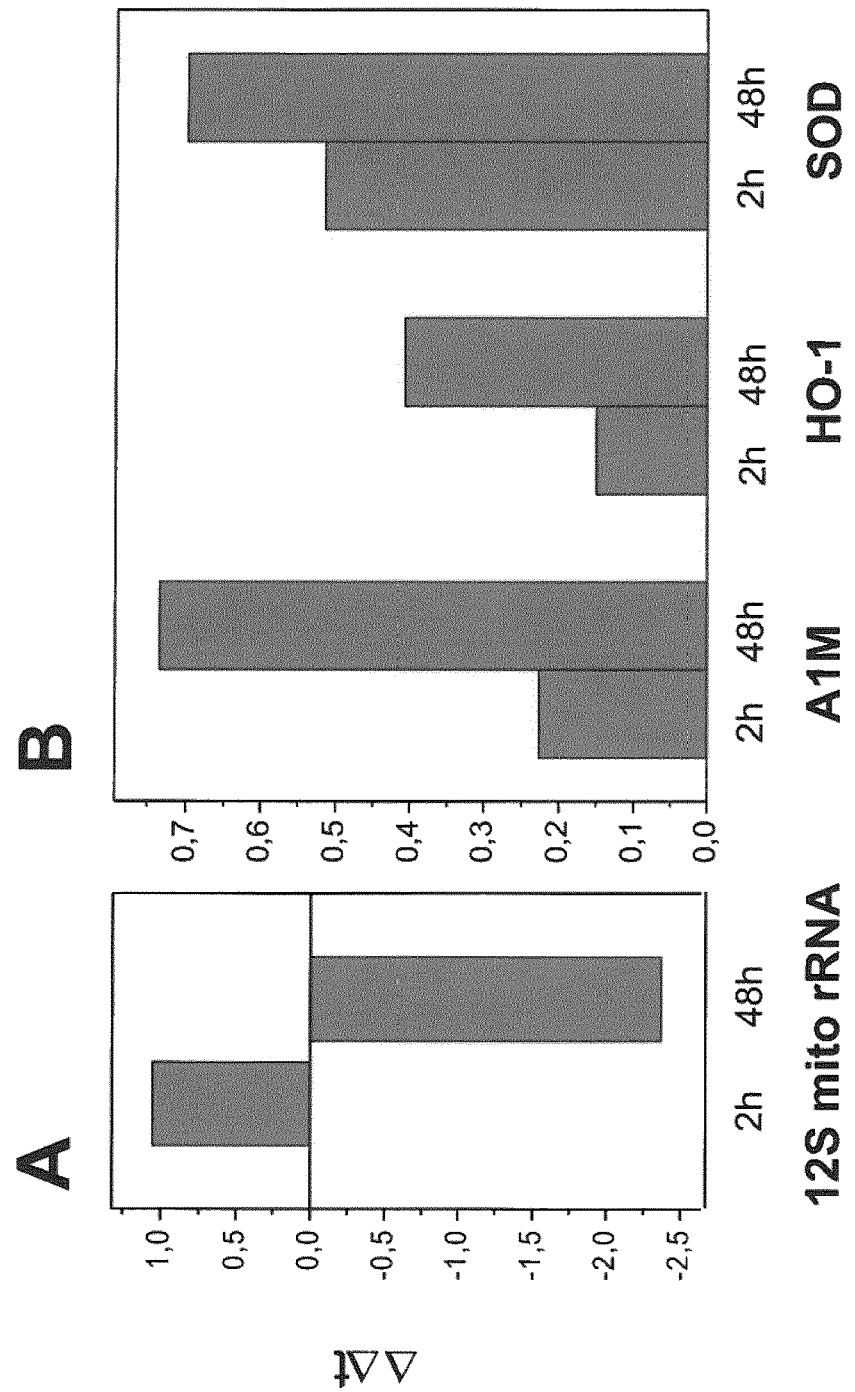

FIG. 10. Realtime PCR quantitation of mitochondrial rRNA (A) and cellular A1M, HO1 and SOD mRNA (B) during retina culture under mild and stress conditions. Each ΔΔt-value corresponds to the amount of RNA in stressed conditions relative to the RNA amount in mild conditions, determined by realtime PCR and normalized to glyceraldehyde-3-phosphate dehydrogenase. Each bar is the mean of duplicate measurements of triplicate cultures.

EXPERIMENTAL

Example 1

Materials and Methods
Proteins and Antibodies

Human monomeric plasma A1M was isolated by anti-A1M affinity chromatography and Sephacryl S-300 gel-chromatography, as described previously (48). Recombinant human A1M, containing an N-terminal His-tag, was purified from the culture medium of baculovirus-infected insect cells (48) or expressed in *E. coli* and purified and refolded as described (20) with the addition of an ion-exchange chromatography purification step (32). Human serum $α_1$-acid glycoprotein (AGP) and ovalbumin were purchased from Sigma-Aldrich Co. (St. Louis, Mo., USA) and bovine serum albumin (BSA) was from Roche Diagnostics Scandinavia AB (Bromma, Sweden). Hemin (Ferriprotoporphyrin IX chloride) was purchased from Porphyrin Products, Inc. (Logan, Utah) and a 10 mM stock solution was prepared fresh by dissolving in dimethyl sulphoxide (DMSO; Sigma-Aldrich). $H_2O_2$ was from Acros Organics (Geel, Belgium). Mouse monoclonal antibodies against human A1M (BN11.3) were raised as described (29). Rabbit polyclonal anti-mouse A1M antibodies (Sven; IgG-fraction) were prepared by immunizing a rabbit with His-tagged mouse A1M expressed in baculovirus-infected insect cells (41). The hamster anti-mouse CD 3 antibody 145.2C11 was kindly provided by Dr. Rikard Holmdahl, Lund University. Fluorescein isothiocyanate-conjugated goat anti-mouse immunoglobulin (GAM-FITC) and phycoerythrein-conjugated streptavidin (SAPE) were purchased from DAKO A/S (Glostrup, Denmark), 7-amino actinomycin D (7 AAD) was from Sigma-Aldrich Co. and annexin V-FITC was from Trevigen Inc. (Gaithersburg, Md., USA).

Cell Culture

A mouse CD4+ T cell hybridoma cell line (HCQ.4), a murine pre-B-cell line (70Z/3), a human erythroid cell line (K562) and human primary keratinocytes (Cambrex Biologics, Karlskoga, Sweden) were employed for studies on A1M binding to cells and mitochondria. Cells were cultivated as described previously (25,28,37) and processed and analyzed as described below.

Induction of Apoptosis

Apoptosis was induced in the T cell hybridoma by three different treatments: Cells were incubated on anti-CD3 antibody coated plastics (4 µg/ml) (43), or incubated in medium supplemented with either 5% ethanol or 10% of DMSO (24). The cells were incubated in a $CO_2$-incubator at 37° C. for various times. Apoptosis was detected as DNA-fragmentation by agarose-gel electrophoresis (described below) and cell viability was measured by trypan blue exclusion. In the pre-B-cell line 70Z/3, apoptosis was induced by the benzamide-drug declopramide (3-CPA, Oxigene Inc.) as described in (25).

Agarose Electrophoresis

To detect DNA fragmentation, approximately $1 \times 10^6$ cells were lysed, proteinase K- and RNAse A-treated and analyzed by agarose electrophoresis.

Labeling of A1M

For analysis of A1M-binding to cells, A1M was biotinylated, FITC conjugated or $^{125}$I radiolabeled. A1M was biotinylated with long arm-biotin N hydroxysuccinimide (Vector Laboratories Inc., Burlingame, Calif., USA) (9) and diluted to a concentration of 0.2 mg/ml. A1M was FITC-conjugated as described previously (13) by FITC adsorbed on Celite (Calbiochem Corp, San Diego, Calif., USA). A1M was labeled with $^{125}$I using the chloramine T method (16). The specific radioactivity obtained was around 0.1-0.2 MBq/µg.

Flow Cytometry

A1M-binding to cells was analyzed by flow cytometry. Approximately $1 \times 10^6$ cells were analyzed for A1M-binding in one of three different ways: 1. The cells were incubated with 1 mg/ml of plasma or recombinant insect cell-A1M, followed by 10 µg/ml of monoclonal mouse anti-A1M (BN 11.3) and GAM-FITC (diluted 20 times). 2. The cells were incubated with 10 µg/ml biotinylated-A1M followed by SAPE (diluted according to the manufacturer's recommendations). 3. The cells were incubated with 0.1 mg/ml FITC-conjugated A1M. All incubations were performed in PBS+1 mg/ml of BSA for 10 minutes at RT. Between the incubations, the cells were washed 2-3 times in PBS. To detect leaking cells, cells were incubated with propidium iodide (PI; Invitrogen Inc.) or 7AAD (according to manufacturers' instructions). To detect apoptotic 70Z/3 cells, cells were also incubated with FITC-conjugated annexin V in a $Ca^{2+}$-containing buffer (according to the manufacturers' instructions). All analyses were performed using a Becton Dickinson FACSorter and the Cell Quest software package.

Fluorescence and Confocal Microscopy

K562 cells were washed and re-suspended in culture medium to $0.5\text{-}4.0 \times 10^6$ cells/ml and incubated with or without A1M as indicated in the figure legends. Cells were then either incubated with Mito-Tracker (Invitrogen Inc.) for 15 minutes at 37° C. and washed in fresh medium (FIG. 3A) or directly washed in fresh medium (FIG. 1C) After washing, staining of the cells was performed by re-suspending in ice-cold Na-medium (5.4 mM KCl; 1.2 mM $KH_2PO_4$; 0.8 mM $MgSO_4$; 5.6 mM D-glucose; 127 mM NaCl; 10 mM Hepes; 1.8 mM $CaCl_2$; pH 7.3), fixation with 1% BD CellFIX on ice for 15 min and at RT for 45 min. Cells were washed in blocking solution (Na-medium; 1% BSA; 5% goat serum) followed by permeabilization in 0.02% Triton-X and blocking in 1% BSA, 5% goat serum, 0.2% Tween-20 for 1 hour at RT. The cells were then stained at 4° C. over-night with monoclonal mouse anti-A1M (BN 11.3) at 5 µg/ml. Subsequently, goat anti-mouse IgG F(ab')$_2$ fragments (Alexa Fluor® 594; Invitrogen Inc.), was applied for 1 h at RT. Cells were mounted using ProLong Gold AntiFade Reagent with DAPI. For fluorescence microscopy, visual inspection and recording of images were performed using a Nikon Eclipse TE300 inverted fluorescence microscope equipped with a Hamamatsu C4742-95 cooled CCD camera, using a Plan Apochromat 100× objective. For confocal microscopy, analyses of cells and fluorescent markers were performed using an epi-fluorescence microscope (Nikon Eclipse TE300) and a confocal laser scanning microscope (Zeiss LSM 510 Meta). The epi-fluorescens microscope was equipped with the appropriate filter combinations to selectively visualize the used fluorophores. Analyses were made using a Plan Apochromat 100× lens, and the image data was collected with a Hamamatsu C4742-95 CCD camera. To analyze intracellular labeling and co-labeling in subcellular structures, confocal scanning of optical sections were recorded through the cells. For excitation of the fluorophores, the 405 nm laser line was used for DAPI (diode laser 405-30), the 488 nm laser line was used for Alexa Fluor 488 (Argon laser), and the 561 nm laser line was used for Mito-Tracker (DPSS 561-10). The individual fluorophore emission wavelengths were detected using the following filters: bandpass 420-480 nm for DAPI, bandpass 505-550 nm for Alexa Fluor 488, and longpass 575 nm for Mitotracker. The pinhole for detection of Alexa Fluor 488 (488 nm excitation) was set to correspond to 1 (one) Airy unit, and the pinholes for the other detection channels were then adjusted to give optical sections of the same thickness, i.e. to ensure comparisons of the corresponding confocal volumes. Laser power and detection settings (gain and offset) were optimized for the individual channels, giving a detection range from highly saturated pixels of larger structures to non-saturated pixels of small structures. The different fluorophores were sequentially scanned, i.e. with optimal settings for one fluorophore in each channel, at 512×512 or 1024×1024 frame size. To determine cellular morphology, differential interpherence contrast (DIC) images were obtained using the 405 nm laser as transmitted light. The spatial relation between the Alexa Fluor 488 fluorescence (green) and Mito-Tracker fluorescence (red) was determined via merging of the optical sections from the individually scanned channels (yellow when co-localized), confirmed via analyses of merged images using the LSM Zen software ("Profile", data not shown).

Yeast 2-Hybrid System

A GAL4-based yeast 2-hybrid system was used to search for A1M-interacting cellular proteins. DNA encoding the A1M-part (amino acids 1-183) of the A1M-bikunin gene (AMBP) was amplified by PCR using a pCR-Script construct as a template. The fragment was completely sequenced and ligated into the yeast 2-hybrid vector pBD-GAL4 Cam phagemid vector (Stratagene, La Jolla, Calif., USA). The recombinant vector was then transformed into the S. cerevisiae yeast host strain YRG-2 (Stratagene). Growth and maintenance of the yeast strains and 2-hybrid assays were performed using standard protocols as recommended by Stratagene and www.umanitoba.ca/faculties/medicine/units/biochem/gietz. Approximately $7.5 \times 10^8$ YRG-2 carrying the bait plasmid, pBD-GAL4-A1M was transformed with 15-20 µg of a human leukocyte MATCH-MAKER cDNA library (Clontech Laboratories, Inc., Palo Alto, Calif., USA). The resulting approximately $2 \times 10^6$ transformants were analyzed by histidine prototrophy assay and β-gal colony lift assay. Recombinant library plasmids from the His$^+$LacZ$^+$ transformants were isolated and retested in direct 2-hybrid assays together with the A1M bait plasmid as well as with bait plasmids encoding unrelated proteins. Plasmids resulting in activation of the reporter genes together with A1M-encoding bait plasmid, but not with the bait plasmids encoding unrelated proteins were regarded as true positives. The DNA sequence of the inserts was determined using the vector primers pAD5':5'-tccagattacgctagct-tgggtggtcatatg-3' (SEQ ID NO: 6) and pAD3':5'-gtgaactt-gcggggtttttcagtatctacga-3' (SEQ ID NO: 7). One of the inserts was sequenced completely by Innovagen AB (Lund, Sweden).

Mitochondria Preparation from Mouse Liver Tissue

Mouse liver tissue was collected in ice cold isolation buffer (320 mM Sucrose, 10 mM Trizma Base, 2 mM EGTA) and subsequently homogenized in 2 ml homogenization buffer (isolation buffer supplemented with 1% BSA). Mitochondria were prepared from homogenates by sequential centrifugation including density purification on 19% Percoll. The protein concentration of mitochondrial preparations was determined using Nanodrop and isolated mitochondria were used without freezing.

Competitive Cell- and Mitochondria-Binding Assay.

The specificity of A1M-binding to cells and mitochondria was investigated by a competitive cell-binding assay as described (3,49). Apoptosis was induced in HCQ.4 cells by anti-CD3 cross-linking for 15-18 hours. The cells were harvested and compared to normal cells in the binding assay. An affinity constant for the binding was calculated using a Scatchard plot of the data.

Immunocapture of Complex I

Immunoprecipitation of Complex I was performed on freshly prepared mitochondria using the Complex I Immunocapture Kit (MitoSciences). Following the immunoprecipitation, bound proteins were eluted using SDS-buffer and subsequently analyzed using SDS-PAGE and Western blotting.

Isolation of Respiratory Chain Complexes and Supercomplexes

Freshly isolated, non-frozen mitochondrial pellets were suspended in PBS supplemented with Complete Mini Protease inhibitor. Mitochondria were pelleted for 5 min at 5000×g and subsequently dissolved to a concentration of 5 mg/ml in MB2 buffer (1.75 M aminocaproic acid, 7.5 mM Bis-Tris pH 7.0, +2 mM EGTA pH 8.0). Mitochondrial membrane proteins were solubilized by incubation with 0.5% digitonin for 5 min on ice. Samples were centrifuged for 30 min at 13000×g, the supernatant was collected and the protein concentration measured as before. Finally, SBG (750 mM aminocaproic acid, 5% Serva Blue G) was added to a final concentration of 4.5%.

Blue Native PAGE, SDS-PAGE and Western Blotting

Five µg mitochondrial membrane proteins were separated on a BN-PAGE 4-16% Bis-Tris gel (Invitrogen Inc.) either stained with Coomassie Brilliant Blue or blotted to a PVDF membrane (Immobilon, Millipore, Bedford, Mass., USA) using Iblot equipment (Invitrogen Inc.). Complex I-immunoprecipitated proteins were separated on a 12% SDS-PAGE and transferred to a PVDF membrane. After blocking over-night at 4° C. the membranes were incubated with antibodies against subunit NDUFV1 of Complex I (Sigma) or mouse A1M. Primary antibodies were detected by incubation with HRP-coupled goat anti-mouse (DAKO) or goat anti-rabbit (DAKO).

Transmission Electron Microscopy (TEM)

Human keratinocytes (about 1 million cells), incubated for 20 hours at RT with 20 µM heme, with or without 10 µM A1M, were pelleted by centrifugation and subsequently fixed for 1 hour at RT and then overnight at 4° C. in 2.5% glutaraldehyde in 0.15 M sodium cacodylate, pH 7.4 (cacodylate buffer). Samples were then washed with cacodylate buffer and post-fixed for 1 hour at RT in 1% osmium tetroxide in cacodylate buffer, dehydrated in a graded series of ethanol, and then embedded in Epon 812 using acetone as an intermediate solvent. Specimens were sectioned with a diamond knife into 50-70 nm-thick ultrathin sections on an LKB ultramicrotome. The ultrathin sections were stained with uranyl acetate and lead citrate. Specimens were observed in a JEOL JEM 1230 electron microscope operated at 80 kV accelerating voltage. Images were recorded with a Gatan Multiscan 791 CCD camera. Immunolabeling of thin sections with gold-labeled anti-A1M (BN11.3) were performed as described previously (39) with the modification that Aurion-BSA was used as a blocking agent. Samples were finally stained with uranyl acetate and lead citrate and observed in a Jeol JEM 1230 electron microscope, operated at 80 kV accelerating voltage. Images were recorded with a Gatan Multiscan 791 charge-coupled device camera.

ATP Assay

Cellular ATP production was measured using a luminescence assay kit (Promega, Madison, Wis.), based on the ATP-dependent activity of luciferase. ATP levels were normalized to the corresponding sample protein content.

Statistical Analysis

Statistical analysis was performed using Origin 8 software. Student's t-test was used for statistical evaluation and was considered significant when $P<0.05$.

Results

Specific Binding of A1M to Damaged Cells

Binding of A1M to apoptotic and healthy cells was analyzed by flow cytometry and compared to untreated cells. First, apoptosis was induced in murine T cell hybridomas (HCQ.4) by cross-linking of the CD3 molecule with immobilized anti-mouse CD3 antibodies (FIGS. 1A, E), or by incubation with 5% ethanol or 10% DMSO (FIG. 1B). These treatments resulted in DNA fragmentation and uptake of trypan blue after 15-18 hours (not shown). A weak binding of A1M could be detected to untreated cells (FIG. 1A, left panel). An additional stronger binding could be detected to cells cross-linked with anti-CD3 (FIG. 1A, right panel) or treated with ethanol or DMSO (FIG. 1B). The binding could be correlated to PI uptake, i.e. only cells that could incorporate PI displayed the stronger binding of A1M (FIG. 1B). Flow cytometry of a murine pre-B-cell line, induced to apoptosis using the drug 3-CPA, and incubated with A1M followed by anti-A1M, showed similar results (FIG. 1C), indicating that the binding to apoptotic cells is not restricted to T cells.

In order to further characterize the A1M binding to damaged cells, the binding was studied using fluorescence microscopy of the human erythroid cell line K562 (FIG. 1D) and the promyelocytic cell line HL 60 (not shown) induced to apoptosis by addition of heme, and incubated with A1M followed by anti-A1M. As illustrated in the figure, two different types of staining could be seen, a weak granular staining to the cell surface of most cells and a more pronounced, intracellular and uniform staining to a subset (approximately 6%) of the cells. Similar results were obtained with the HL 60 cells (not shown). These results indicate that the strong binding of A1M to apoptotic cells is mainly intracellular, which was confirmed by confocal microscopy (see below; FIG. 3A).

To investigate the specificity of the binding, a competitive cell-binding assay was performed on HCQ.4 cells, induced to apoptosis by CD3 cross-linking and compared to normal untreated cells. $^{125}$I-labeled A1M and an excess of unlabeled A1M, ovalbumin, BSA or AGP were added to the cells (FIG. 1E). More A1M was bound to apoptotic cells (FIG. 1E, left) compared to untreated cells (right). Excess of unlabeled A1M blocked the $^{125}$I-A1M binding to the same basal level for apoptotic cells as for untreated cells. The reduction was found to be significant (p<0.001). None of the unlabeled control proteins could significantly reduce the binding of $^{125}$I-A1M to untreated cells, thus indicating a specific binding of A1M. To the apoptotic cells, there was a small, significant reduction by the control proteins (p<0.05). This small reduction may be due to an increased unspecific background binding to exposed intracellular structures. Accordingly, the results indicate a specific stronger binding of A1M to apoptotic cells. From a Scatchard plot an affinity constant for the A1M binding to apoptotic HCQ.4 cells could be determined to $1\times10^6$ M$^{-1}$. The viability of these cells was 25% according to trypan blue exclusion (not shown).

As mentioned above, the A1M-binding cells internalized PI (FIG. 1B). This indicates that the A1M-binding occurred late in the apoptotic process after the cell membranes had started to leak. To confirm this result, time studies on the binding of A1M to HCQ.4 cells, induced to apoptosis by anti-CD3 cross-linking, were performed. Flow cytometry of samples taken at various time-points after induction shows that the PI uptake precedes the binding of A1M (FIG. 2A). The clear binding correlation was not seen to cells negative for PI uptake. The same result was obtained when the murine pre-B-cells were triple-stained with A1M, annexin V (marker for apoptosis) and 7AAD (marker dye for cell membrane permeability) (FIG. 2B). Only 7AAD positive cells showed a strong A1M binding, whereas cells positive for annexin V, but not for 7AAD, did not bind A1M.

Identification of Intracellular A1M-Binding Proteins

To search for cellular proteins interacting with A1M, the yeast 2-hybrid system was used. cDNA coding for A1M was used as a bait to search for A1M-interacting proteins in a human leukocyte library. Approximately $2\times10^6$ transformants were analyzed for reporter gene activation. A total of 168 colonies survived on plates lacking histidine and 13 of them were also positive for 13-galactosidase. The His$^+$ LacZ$^+$ recombinant library plasmids were isolated and tested in direct 2-hybrid assays with bait plasmids encoding only the bait protein as well as the protein fused to unrelated proteins. Eleven recombinant plasmids were shown to encode proteins that interacted with A1M, but not with the bait protein or other unrelated proteins fused to it. DNA sequencing of the inserts revealed that seven of them were a truncated form of the SDAP subunit (NDUFAB1) in mitochondrial Complex I, one was the complete sequence of the same subunit, one was a snRNA binding protein, one was N-acetylglucosamine kinase and one was a colon cancer antigen. All inserts were in frame in the prey vector (Table I).

TABLE 1

A1M interacting proteins found in the yeast-two hybrid system.

| Protein | No. of colonies | Genebank Accession No. | Bases No.* |
|---|---|---|---|
| NADH dehydrogenase 8 kDa, SDAP subunit (NDUFAB1) | 7 | NM_005003 | 142-670 |
| NADH dehydrogenase 8 kDa, SDAP subunit (NDUFAB1) | 1 | NM_005003 | 18-670 |
| U6 snRNA-associated Sm-like protein (LSM5) | 1 | AF182291 | 14-735 |
| N-acetylglucosamine kinase (NAGK) | 1 | AJ242910 | 7-1187 |
| Serologically defined colon cancer antigen 3, NY-CO-3 (SDCCAG3) | 1 | AK001296 | 0-1441 |

*According to the base numbering of the Genebank Accession No. assigned in this table.

Binding of A1M to Mitochondrial Complex I

The results from the yeast 2-hybrid experiments thus suggest that a subunit of mitochondrial Complex I is a major A1M-binding intracellular protein. Binding to mitochondria, and to Complex I in particular, was therefore investigated in detail using several independent methods: confocal microscopy, EM, subcellular fractionation, and PAGE. Using a mitochondrial fluorescent probe (Mito-Tracker) and confocal microscopy we evaluated the subcellular localization of the intracellular A1M in K562 cells with or without addition of exogenous A1M (FIG. 3A). Analyzing cells without exogenously added A1M a very weak unspecific intracellular staining was observed (not shown). However, with the addition of exogenous A1M an intense, mitochondria-specific staining was observed. The subcellular localization of the bound A1M was also studied by Transmission EM (TEM) using primary human keratinocyte cultures (FIG. 3B-C). TEM of keratinocytes, containing exogenously added A1M and incubated with gold-labeled anti-A1M, showed a highly specific localization of A1M to the mitochondria (FIG. 3C).

Confirmation of mitochondrial binding and verification of specificity was performed using purified mitochondria from mouse liver (FIG. 4A). $^{125}$I-labeled A1M was incubated with the mitochondria, with or without an excess of unlabeled A1M or the control protein AGP. Excess of unlabeled A1M blocked the $^{125}$I-A1M binding significantly at the two higher concentrations, whereas AGP at the highest concentration had no effect on the binding. Scatchard analysis of the binding data yielded an affinity constant of the binding at $1.2\times10^6$ M$^{-1}$.

To investigate if endogenous A1M is found in mitochondria associated with Complex I, mouse mitochondria were purified without freezing, solubilized, separated under nondenaturing conditions, and analyzed by Western blotting using antibodies against subunits of Complex I and III (denoted NDUFV1 and Core I, respectively) and against mouse A1M (FIG. 4B). The results show that A1M co-migrates with the major Complex I-containing band and a supercomplex-band containing both Complex I and III, whereas no co-migration was seen between A1M and the major Complex III-containing band. Taken together, this support a specific association between A1M and a Complex I subunit. However, a large fraction of A1M migrated at a position corresponding to approximately 350-400 kDa, suggesting that A1M is also associated with other, as yet unidentified, large structures in mitochondria. The blotting intensity of all bands decreased with increasing digitonin concentrations, suggesting that all bands seen in the gels results from non-covalent protein-protein interactions (FIG. 5A). The binding between A1M and Complex I was confirmed by anti-Complex I immunoprecipitation followed by blotting with anti-A1M (FIG. 4C). The results showed that the majority of mitochondria-associated A1M positive bands in the starting material (FIG. 4C, left) were precipitated. Also, a new band, not detectable in the starting material, was seen in the immunoprecipitate. Trypsin digestion of intact mitochondria before SDS-PAGE and blotting with anti-A1M did not decrease the amount of A1M found in the mitochondria, supporting a localization of A1M in the inner mitochondrial membrane (FIG. 5B).

A1M Protects Mitochondrial Structure and Function

Hypothesizing that the physiological role of mitochondrial-bound A1M is to confer protection of this organelle, we first employed TEM to investigate the impact of A1M on the structure of mitochondria in cells exposed to heme and $H_2O_2$ (FIGS. 6 and 7). TEM was performed on cultured human primary keratinocytes. Extensive destructive effects were seen by heme (FIG. 6B) and $H_2O_2$ (FIG. 7B), i.e. vast formation of vacuoles, structural des-organization of keratin fibres and swelling of the mitochondria (FIGS. 6B and 7B, zoomed in). These effects were counteracted by the addition of A1M, where a particular impact was seen on the mitochondrial swelling (FIGS. 6C and 7C, zoomed in). The results suggest that A1M protects and preserves cellular structures otherwise damaged and disintegrated.

We next investigated the effects of A1M on mitochondrial function by measuring ATP-production of purified mitochondria exposed to heme or $H_2O_2$ (FIG. 8). A significant reduction in the rate of ATP-production was seen by 5 and 20 μM heme (FIG. 8A). This reduction was reversed by A1M, and no reduction in ATP-production rate was seen by heme in any of the tested concentrations when 10 μM A1M was present. Similar results were obtained using $H_2O_2$ (FIG. 8B). Thus, $H_2O_2$ significantly reduced the rate of ATP-production, but the effects were significantly reversed in the presence of 10 μM A1M.

Example 2. Stress Conditions in Retina Cultures Induce Structural and Functional Damage of Mitochondria, Cellular Antioxidation Response and Cellular A1M Up-Regulation Methods Pig retinas were dissected and cultured in Petri dishes under mild and stress conditions in vitro as described for rat retinas (Cederlund M, Ghosh F, Arner K, Andreasson S, Åkerström B. Vitrous levels of oxidative stress biomarkers and the radical scavenger alpha-1-microglobulin/A1M in human rhegmatogenous retinal detachment. Graefe's Arch Clin Exp Ophtalmol (2013) 251: 725-732). After 2 h or 48 h, mRNA was isolated and quantitated, cDNA synthesized by reversed transcription and the amount of specific sequences quantitated by realtime PCR. The obtained amounts of each mRNA species in stressed cultures were normalized to mRNA from the housekeeping gene glyceraldehyde-3-phosphate-dehydrogenase and expressed in relation to the normalized genes in non-stressed conditions (ΔΔCt).

Results

The expression of mitochondria-specific ribosomal RNA (12S rRNA) was dramatically down regulated in retinas cultured 48h under stress conditions as compared to mild conditions (FIG. 10a), suggesting damage to mitochondrial structure and function. At the same time, the A1M-gene and the two antioxidation genes heme oxygenase 1 (HO1) and superoxide dismutase (SOD) were up regulated in stressed cultures as compared to mild cultures after both 2 h and 48 h (FIG. 10b), suggesting that retina cellular defense mechanisms including A1M are activated.

CONCLUSIONS

Retinal stress during in vitro culture negatively affects retinal mitochondrial structure and function and upregulates antioxidation defense and A1M-expression. These results support a role of A1M in mitochondrial protection during retinal culture.

LIST OF ABBREVIATIONS

Reactive oxygen species ROS
Hemoglobin Hb
Superoxide dismutase SOD
Glutathione peroxidase GPx
$\alpha_1$-microglobulin A1M
Violaxanthin-deepoxidase VDE
Zeaxtanthin epoxidase ZDE
$\alpha_1$-acid glycoprotein AGP
Bovine serum albumin BSA
Dimethyl sulphoxide DMSO
Fluorescein isothiocyanate-conjugated GAM-FITC goat anti-mouse immunoglobulin
Phycoerythrein-conjugated streptavidin SAPE
7-amino actinomycin D 7 AAD

REFERENCES

1. Allhorn M, Berggård T, Nordberg J, Olsson M L and Åkerström B. Processing of the lipocalin a₁-microglobulin by hemoglobin induces heme-binding and heme-degradation properties. *Blood* 99: 1894-901, 2002.
2. Allhorn M, Klapyta A and Åkerström B. Redox properties of the lipocalin a₁-microglobulin: reduction of cytochrome c, hemoglobin, and free iron. *Free Radic Biol Med* 38: 557-67, 2005.
3. Babiker-Mohamed H, Olsson M L, Boketoft A, Lögdberg L and Åkerström B. a₁-microglobulin is mitogenic to human peripheral blood lymphocytes. Regulation by both enhancing and suppressive serum factors. *Immunobiology* 180: 221-34, 1990.
4. Berggård T, Oury T D, Thogersen I B, Åkerström B and Enghild J J. a₁-microglobulin is found both in blood and in most tissues. *J Histochem Cytochem* 46: 887-94, 1998.
5. Berggård T, Thelin N, Falkenberg C, Enghild J J and Åkerström B. Prothrombin, albumin and immunoglobulin A form covalent complexes with a₁-microglobulin in human plasma. *Eur J Biochem* 245: 676-83, 1997.

6. Brand M D. The sites and topology of mitochondrial superoxide production. *Exp Gerontol* 45: 466-72, 2010.
7. Degterev A and Yuan J. Expansion and evolution of cell death programmes. *Nat Rev Mol Cell Biol* 9: 378-90, 2008.
8. DeMars D D, Katzmann J A, Kimlinger T K, Calore J D and Tracy R P. Simultaneous measurement of total and IgA-conjugated $a_1$-microglobulin by a combined immunoenzyme/immunoradiometric assay technique. *Clin Chem* 35: 766-72, 1989.
9. Elbashir M I, Nilson B H, Akesson P, Bjorck L and Åkerström B. Antibody response in immunized rabbits measured with bacterial immunoglobulin-binding proteins. *J Immunol Methods* 135: 171-9, 1990.
10. Faivre B, Menu P, Labrude P and Vigneron C. Hemoglobin autooxidation/oxidation mechanisms and methemoglobin prevention or reduction processes in the bloodstream. Literature review and outline of autooxidation reaction. *Artif Cells Blood Substit Immobil Biotechnol* 26: 17-26, 1998.
11. Flower D R. The lipocalin protein family: structure and function. *Biochem J* 318 (Pt 1): 1-14, 1996.
12. Ganfornina L, Sanchez D, Greene L H and Flower D R. The lipocalin protein family. Protein sequence, structure and relationship to calycin superfamily. In: *Lipocalins*. edited by Åkerström B, Borregaard N, Flower D R and Salier J P. Georgetown, Tex.: Landes Bioscience; 2006. pp. 17-27.
13. Goding J W. *Monoclonal Antibodies: Principles and Practice*. (Orlando, Fla.: Academic Press; 1986.
14. Goss R and Jakob T. Regulation and function of xanthophyll cycle-dependent photoprotection in algae. *Photosynth Res* 106: 103-22, 2010.
15. Gray M W, Burger G and Lang B F. Mitochondrial evolution. *Science* 283: 1476-81, 1999.
16. Greenwood F C, Hunter W M and Glover J S. The Preparation of I-131-Labelled Human Growth Hormone of High Specific Radioactivity. *Biochem J* 89: 114-23, 1963.
17. Halliwell B and Gutteridge J M. *Free Radicals in Biology and Medicine*. (4th ed) Oxford: Oxford University Press; 2007.
18. Hinderlich S, Berger M, Schwarzkopf M, Effertz K and Reutter W. Molecular cloning and characterization of murine and human N-acetylglucosamine kinase. *Eur J Biochem* 267: 3301-8, 2000.
19. Kastern W, Björck L and Åkerström B. Developmental and tissue-specific expression of $a_1$-microglobulin mRNA in the rat. *J Biol Chem* 261: 15070-4, 1986.
20. Kwasek A, Osmark P, Allhorn M, Lindqvist A, Akerstrom B and Wasylewski Z. Production of recombinant human alpha1-microglobulin and mutant forms involved in chromophore formation. *Protein Expr Purif* 53: 145-52, 2007.
21. Larsson J, Allhorn M and Åkerström B. The lipocalin $a_1$-microglobulin binds heme in different species. *Arch Biochem Biophys* 432: 196-204, 2004.
22. Larsson J, Wingårdh K, Berggård T, Davies J R, Lögdberg L, Strand S E and Åkerström B. Distribution of iodine $^{125}$-labeled $a_1$-microglobulin in rats after intravenous injection. *J Lab Clin Med* 137: 165-75, 2001.
23. Lee J, Giordano S and Zhang J. Autophagy, mitochondria and oxidative stress: cross-talk and redox signalling. *Biochem J* 441: 523-40, 2012.
24. Lennon S V, Martin S J and Cotter T G. Dose-dependent induction of apoptosis in human tumour cell lines by widely diverging stimuli. *Cell Prolif* 24: 203-14, 1991.
25. Liberg D, Lazarevic B, Pero R W and Leanderson T. N-substituted benzamides inhibit NFkappaB activation and induce apoptosis by separate mechanisms. *Br J Cancer* 81: 981-8, 1999.
26. Loschen G, Azzi A and Flohe L. Mitochondrial H2O2 formation: relationship with energy conservation. *FEBS Lett* 33: 84-7, 1973.
27. May K, Rosenlöf L, Olsson M G, Centlow M, Mörgelin M, Larsson I, Cederlund M, Rutardóttir S, Siegmund W, Schneider H, Åkerström B and Hansson S R. Perfusion of human placenta with hemoglobin introduces preeclampsia-like injuries that are prevented by $a_1$-microglobulin. *Placenta* 32: 323-32, 2011.
28. Michaelsson E, Malmström V, Reis S, Engström A, Burkhardt H and Holmdahl R. T cell recognition of carbohydrates on type II collagen. *J Exp Med* 180: 745-9, 1994.
29. Nilson B, Åkerström B and Lögdberg L. Cross-reacting monoclonal anti-$a_1$-microglobulin antibodies produced by multi-species immunization and using protein G for the screening assay. *J Immunol Methods* 99: 39-45, 1987.
30. Nisbet E G and Sleep N H. The habitat and nature of early life. *Nature* 409: 1083-91, 2001.
31. Olsson M G, Allhorn M, Bulow L, Hansson S R, Ley D, Olsson M L, Schmidtchen A and Åkerström B. Pathological conditions involving extracellular hemoglobin: molecular mechanisms, clinical significance, and novel therapeutic opportunities for $a_1$-microglobulin. *Antioxid Redox Signal* In press, 2012.
32. Olsson M G, Allhorn M, Larsson J, Cederlund M, Lundqvist K, Schmidtchen A, Sorensen O E, Mörgelin M and Åkerström B. Up-regulation of A1M/$a_1$-microglobulin in skin by heme and reactive oxygen species gives protection from oxidative damage. *PLoS One* 6: e27505, 2011.
33. Olsson M G, Allhorn M, Olofsson T and Åkerström B. Up-regulation of $a_1$-microglobulin by hemoglobin and reactive oxygen species in hepatoma and blood cell lines. *Free Radic Biol Med* 42: 842-51, 2007.
34. Olsson M G, Centlow M, Rutardóttir S, Stenfors I, Larsson J, Hosseini-Maaf B, Olsson M L, Hansson S R and Åkerström B. Increased levels of cell-free hemoglobin, oxidation markers, and the antioxidative heme scavenger $a_1$-microglobulin in preeclampsia. *Free Radic Biol Med* 48: 284-91, 2010.
35. Olsson M G, Nilsson E J, Rutardottir S, Paczesny J, Pallon J and Åkerström B. Bystander Cell Death and Stress Response is Inhibited by the Radical Scavenger $a_1$-Microglobulin in Irradiated Cell Cultures. *Radiat Res*, 2010.
36. Olsson M G, Olofsson T, Tapper H and Åkerström B. The lipocalin $a_1$-microglobulin protects erythroid K562 cells against oxidative damage induced by heme and reactive oxygen species. *Free Radic Res* 42: 725-36, 2008.
37. Paige C J, Kincade P W and Ralph P. Murine B cell leukemia line with inducible surface immunoglobulin expression. *J Immunol* 121: 641-7, 1978.
38. Poyton R O, Ball K A and Castello P R. Mitochondrial generation of free radicals and hypoxic signaling. *Trends Endocrinol Metab* 20: 332-40, 2009.
39. Roth J. Post-embedding cytochemistry with gold-labelled reagents: a review. *J Microsc* 143: 125-37, 1986.
40. Salgado-Garrido J, Bragado-Nilsson E, Kandels-Lewis S and Seraphin B. Sm and Sm-like proteins assemble in two related complexes of deep evolutionary origin. *EMBO J* 18: 3451-62, 1999.

41. Sanchez D, Martinez S, Lindqvist A, Åkerström B and Falkenberg C. Expression of the AMBP gene transcript and its two protein products, $a_1$-microglobulin and bikunin, in mouse embryogenesis. *Mech Dev* 117: 293-8, 2002.
42. Scanlan M J, Chen Y T, Williamson B, Gure A O, Stockert E, Gordan J D, Tureci O, Sahin U, Pfreundschuh M and Old L J. Characterization of human colon cancer antigens recognized by autologous antibodies. *Int J Cancer* 76: 652-8, 1998.
43. Shi Y F, Szalay M G, Paskar L, Sahai B M, Boyer M, Singh B and Green D R. Activation-induced cell death in T cell hybridomas is due to apoptosis. Morphologic aspects and DNA fragmentation. *J Immunol* 144: 3326-33, 1990.
44. Tejler L, Eriksson S, Grubb A and Astedt B. Production of protein HC by human fetal liver explants. *Biochim Biophys Acta* 542: 506-14, 1978.
45. Triepels R, Smeitink J, Loeffen J, Smeets R, Buskens C, Trijbels F and van den Heuvel L. The human nuclear-encoded acyl carrier subunit (NDUFAB1) of the mitochondrial complex I in human pathology. *J Inherit Metab Dis* 22: 163-73, 1999.
46. Vandenabeele P, Galluzzi L, Vanden Berghe T and Kroemer G. Molecular mechanisms of necroptosis: an ordered cellular explosion. *Nat Rev Mol Cell Biol* 11: 700-14, 2010.
47. Weisiger R A and Fridovich I. Mitochondrial superoxide simutase. Site of synthesis and intramitochondrial localization. *J Biol Chem* 248: 4793-6, 1973.
48. Wester L, Johansson M U and Åkerström B. Physicochemical and biochemical characterization of human $a_1$-microglobulin expressed in baculovirus-infected insect cells. *Protein Expr Purif* 11: 95-103, 1997.
49. Wester L, Michaelsson E, Holmdahl R, Olofsson T and Åkerström B. Receptor for $a_1$-microglobulin on T lymphocytes: inhibition of antigen-induced interleukin-2 production. *Scand J Immunol* 48: 1-7, 1998.
50. Xiong J, Fischer W M, Inoue K, Nakahara M and Bauer C E. Molecular evidence for the early evolution of photosynthesis. *Science* 289: 1724-30, 2000.
51. Åkerström B, Flower D R and Salier J P. Lipocalins: unity in diversity. *Biochim Biophys Acta* 1482: 1-8, 2000.
52. Åkerström B and Lögdberg L. $a_1$-microglobulin. In: *In: Lipocalins.* edited by Åkerström B, Borregaard N, Flower D R and Salier J-P. Georgetown, Tex., USA: Landes Bioscience; 2006. pp. 110-20.
53. Åkerström B, Maghzal G J, Winterbourn C C and Kettle A J. The lipocalin $a_1$-microglobulin has radical scavenging activity. *J Biol Chem* 282: 31493-503, 2007.

SEQUENCE LISTING

```
<160> NUMBER OF SEQ ID NOS: 7

<210> SEQ ID NO 1
<211> LENGTH: 183
<212> TYPE: PRT
<213> ORGANISM: Homo sapiens

<400> SEQUENCE: 1

Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180
```

<210> SEQ ID NO 2
<211> LENGTH: 201
<212> TYPE: PRT
<213> ORGANISM: Homo sapiens

<400> SEQUENCE: 2

Met His His His His His His His Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
        35                  40                  45

Gly Ser Thr Cys Pro Trp Leu Lys Lys Ile Met Asp Arg Met Thr Val
    50                  55                  60

Ser Thr Leu Val Leu Gly Glu Gly Ala Thr Glu Ala Glu Ile Ser Met
65                  70                  75                  80

Thr Ser Thr Arg Trp Arg Lys Gly Val Cys Glu Glu Thr Ser Gly Ala
                85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
        115                 120                 125

Tyr Ala Ile Phe Leu Thr Lys Lys Phe Ser Arg His His Gly Pro Thr
    130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
        195                 200

<210> SEQ ID NO 3
<211> LENGTH: 549
<212> TYPE: DNA
<213> ORGANISM: Homo sapiens

<400> SEQUENCE: 3
ggccctgtgc caacgccgcc cgacaacatc caagtgcagg aaaacttcaa tatctctcgg      60
atctatggga gtggtacaa cctggccatc ggttccacct gccctggct gaagaagatc      120 atggacagga tgacagtgag cacgctggtg ctgggagagg gcgctacaga ggcggagatc      180
agcatgacca gcactcgttg gcggaaaggt gtctgtgagg agacgtctgg agcttatgag      240
aaaacagata ctgatgggag gtttctctat cacaaatcca aatggaacat aaccatggag      300
tcctatgtgg tccacaccac ctatgatgag tatgccattt ttctgaccaa gaaattcagc      360
cgccatcatg gacccaccat tactgccaag ctctacgggc gggcgccgca gctgagggaa      420
actctcctgc aggacttcag agtggttgcc cagggtgtgg gcatccctga ggactccatc      480
ttcaccatgg ctgaccgagg tgaatgtgtc cctggggagc aggaaccaga gcccatctta      540
atcccgaga                                                             549

<210> SEQ ID NO 4
<211> LENGTH: 603
<212> TYPE: DNA

```
<213> ORGANISM: Homo sapiens

<400> SEQUENCE: 4
atgcatcacc atcaccatca ccatcacggt ggaggagggg gtatcgaggg ccgcggccct    60
gtgccaacgc cgcccgacaa catccaagtg caggaaaact tcaatatctc tcggatctat   120
gggaagtggt acaacctggc catcggttcc acctgcccct ggctgaagaa gatcatggac   180
aggatgacag tgagcacgct ggtgctggga gagggcgcta cagaggcgga gatcagcatg   240
accagcactc gttggcggaa aggtgtctgt gaggagacgt ctggagctta tgagaaaaca   300
gatactgatg ggaggtttct ctatcacaaa tccaaatgga acataaccat ggagtcctat   360
gtggtccaca ccacctatga tgagtatgcc attttttctga ccaagaaatt cagccgccat   420
catggaccca ccattactgc caagctctac gggcgggcgc cgcagctgag ggaaactctc   480
ctgcaggact tcagagtggt tgcccagggt gtgggcatcc ctgaggactc catcttcacc   540
atggctgacc gaggtgaatg tgtccctggg gagcaggaac cagagcccat cttaatcccg   600
aga                                                                 603

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide for silencing expression of
      alpha-1-microglobulin

<400> SEQUENCE: 5
ccuauguggu ccacaccaa                                                 19

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tccagattac gctagcttgg gtggtcatat g                                   31

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtgaacttgc ggggtttttc agtatctacg a                                   31
```

The invention claimed is:

1. A method for treating a mitochondria disease or disorder comprising administering alpha-1-microglobulin (A1M) to a subject in need thereof,
   wherein the A1M is a peptide having an amino acid sequence selected from the group consisting of (a) an amino acid sequence that is at least 80% identical to SEQ ID NO:1 and comprises residues corresponding to Y22, C34, K92, K118, K130, Y132, L180, I181, P182, and R183 of SEQ ID NO:1; and (b) an amino acid sequence that is at least 80% identical to SEQ ID NO:2, and comprises residues corresponding to Y40, C52, K110, K136, K148, Y150, L198, I199, P200, and R201 of SEQ ID NO:2;
   wherein the A1M is the only therapeutic agent administered to the subject to treat the mitochondria disease or disorder; and
   wherein the mitochondria disease or disorder is a Respiratory Chain Deficiency involving Complex I defects or Respiratory Chain Disorder involving Complex I defects.

2. The method according to claim 1, wherein the subject is a child or young adult.

3. The method according to claim 1, wherein the method is for treating one or more Respiratory Chain Deficiency-associated conditions or Respiratory Chain Disorders involving Complex I defects selected from the group consisting of Alpers disease (Progressive Infantile Poliodystrophy), Friedreich's ataxia, KSS, Leigh Disease or Syndrome, Leber's hereditary optic neuropathy (LHON), Mitochondrial Encephalomyopathy Lactic Acidosis and Strokelike Episodes (MELAS), Myoclonic Epilepsy and Ragged-Red Fiber Disease (MERRF), and Neuropathy, Ataxia, and Retinitis Pigmentosa (NARP).

4. The method according to claim 1, wherein the subject is a woman.

5. The method according to claim 1, wherein the method is for treating damage or dysfunction of retina or ocular diseases associated with mitochondrial defect(s) or dysfunction(s).

6. The method according to claim 1, wherein the subject is a human.

7. The method according to claim 1, wherein the method is for treating Friedreich's ataxia.

8. A method for reducing the risk of one or more conditions selected from the group consisting of a mitochondrial defect, a mitochondria disease or disorder, a drug-induced mitochondria side-effect or an environmentally induced mitochondria effect, comprising administering alpha-1-microglobulin (A1M) to a subject in need thereof,
wherein the A1M is a peptide having an amino acid sequence selected from the group consisting of (a) an amino acid sequence that is at least 80% identical to SEQ ID NO:1 and comprises residues corresponding to Y22, C34, K92, K118, K130, Y132, L180, I181, P182, and R183 of SEQ ID NO:1; and (b) an amino acid sequence that is at least 80% identical to SEQ ID NO:2, and comprises residues corresponding to Y40, C52, K110, K136, K148, Y150, L198, I199, P200, and R201 of SEQ ID NO:2;
wherein the A1M is the only therapeutic agent administered to the subject; and
wherein the subject is suffering from a Respiratory Chain Deficiency involving Complex I defects or Respiratory Chain Disorder involving Complex I defects.

9. The method according to claim 8, wherein the subject is a human.

10. The method according to claim 8, wherein the method is for reducing the risk of one or more Respiratory Chain Deficiency-associated conditions or Respiratory Chain Disorders involving Complex I defects selected from Alpers disease (Progressive Infantile Poliodystrophy), Friedreich's ataxia, KSS, Leigh Disease or Syndrome, Leber's hereditary optic neuropathy (LHON), Mitochondrial Encephalomyopathy Lactic Acidosis and Strokelike Episodes (MELAS), Myoclonic Epilepsy and Ragged-Red Fiber Disease (MERRF), and Neuropathy, Ataxia, and Retinitis Pigmentosa (NARP).

11. The method according to claim 8, wherein the method is for reducing the risk of Friedreich's ataxia.

12. The method according to claim 8, wherein the method is for treating damage or dysfunction of retina or ocular diseases associated with mitochondrial defect(s) or dysfunction(s).

* * * * *